(12) United States Patent
Catani et al.

(10) Patent No.: US 12,396,858 B2
(45) Date of Patent: Aug. 26, 2025

(54) TIBIAL BASEPLATE FOR TIBIAL COMPONENT OF A KNEE PROSTHESIS, TIBIAL COMPONENT COMPRISING THE TIBIAL BASEPLATE AND METHOD FOR MANUFACTURING THE TIBIAL BASEPLATE

(71) Applicant: LIMACORPORATE S.P.A., Villanova di San Daniele del Friuli (IT)

(72) Inventors: Fabio Catani, Bologna (IT); Ivan De Martino, Rome (IT); Christoph Fiedler, Diekhof (DE); Joseph D. Lipman, New York, NY (US); Darrick Lo, Brooklyn, NY (US); Michele Pressacco, Martignacco (IT); Fernando J. Quevedo Gonzalez, New York, NY (US); Peter K. Sculco, Brooklyn, NY (US); Thomas P Sculco, New York, NY (US); Timothy M. Wright, New York, NY (US)

(73) Assignee: LIMACORPORATE S P.A., Udine (IT)

( * ) Notice: Subject to any disclaimer, the term of this patent is extended or adjusted under 35 U.S.C. 154(b) by 590 days.

(21) Appl. No.: 17/460,113

(22) Filed: Aug. 27, 2021

(65) Prior Publication Data

US 2021/0386553 A1    Dec. 16, 2021

Related U.S. Application Data

(63) Continuation of application No. PCT/EP2020/054937, filed on Feb. 25, 2020.

(30) Foreign Application Priority Data

Feb. 28, 2019 (EP) ..................................... 19160133
Mar. 19, 2019 (EP) ..................................... 19163638

(51) Int. Cl.
*A61F 2/38* (2006.01)
*A61B 17/15* (2006.01)
(Continued)

(52) U.S. Cl.
CPC .......... *A61F 2/3868* (2013.01); *A61B 17/157* (2013.01); *A61F 2/3094* (2013.01);
(Continued)

(58) Field of Classification Search
CPC ................... A61F 2/3868; A61F 2/389; A61F 2002/30878; A61F 2002/30891;
(Continued)

(56) References Cited

U.S. PATENT DOCUMENTS

2009/0084491 A1* 4/2009 Uthgenannt ............ A61L 27/06
156/153
2010/0298950 A1* 11/2010 McDonnell ........... A61F 2/3662
623/23.53

(Continued)

FOREIGN PATENT DOCUMENTS

| EP | 2319460 | 5/2011 |
|---|---|---|
| EP | 3470020 | 4/2019 |
| JP | 2811450 | 10/1998 |

*Primary Examiner* — Javier G Blanco
(74) *Attorney, Agent, or Firm* — Eversheds Sutherland (US) LLP

(57) ABSTRACT

A tibial baseplate for tibial component of a knee prosthesis including: a bulk solid portion including a proximally facing surface adapted to accommodate a bearing element for the articulation of a femoral component of the knee prosthesis; a plurality of porous portions integral with the bulk solid portion having a porous portion contacting surface opposite to the proximally facing surface adapted to contact a proximal tibia. Advantageously, the plurality of porous portions are seamlessly incorporated and embedded in the bulk solid portion.

15 Claims, 19 Drawing Sheets

(51) Int. Cl.
*A61F 2/30* (2006.01)
*A61F 2/46* (2006.01)

(52) U.S. Cl.
CPC ..... *A61F 2/461* (2013.01); *A61F 2002/30011* (2013.01); *A61F 2002/30978* (2013.01); *A61F 2002/30985* (2013.01); *A61F 2002/4619* (2013.01); *A61F 2310/00023* (2013.01)

(58) Field of Classification Search
CPC .... A61F 2002/3092; A61F 2002/30985; A61F 2002/30736; A61F 2002/3093
See application file for complete search history.

(56) References Cited

U.S. PATENT DOCUMENTS

| | | | |
|---|---|---|---|
| 2011/0035018 A1* | 2/2011 | Deffenbaugh | A61F 2/4202 623/20.14 |
| 2011/0190898 A1* | 8/2011 | Lenz | A61F 2/38 623/20.32 |
| 2011/0313532 A1* | 12/2011 | Hunt | A61F 2/46 623/18.11 |
| 2013/0204384 A1* | 8/2013 | Hensley | A61F 2/389 623/20.35 |
| 2014/0257507 A1* | 9/2014 | Wang | A61F 2/389 623/20.34 |
| 2016/0374829 A1 | 12/2016 | Vogt et al. | |
| 2017/0290668 A1* | 10/2017 | Zajac | A61F 2/389 |

\* cited by examiner

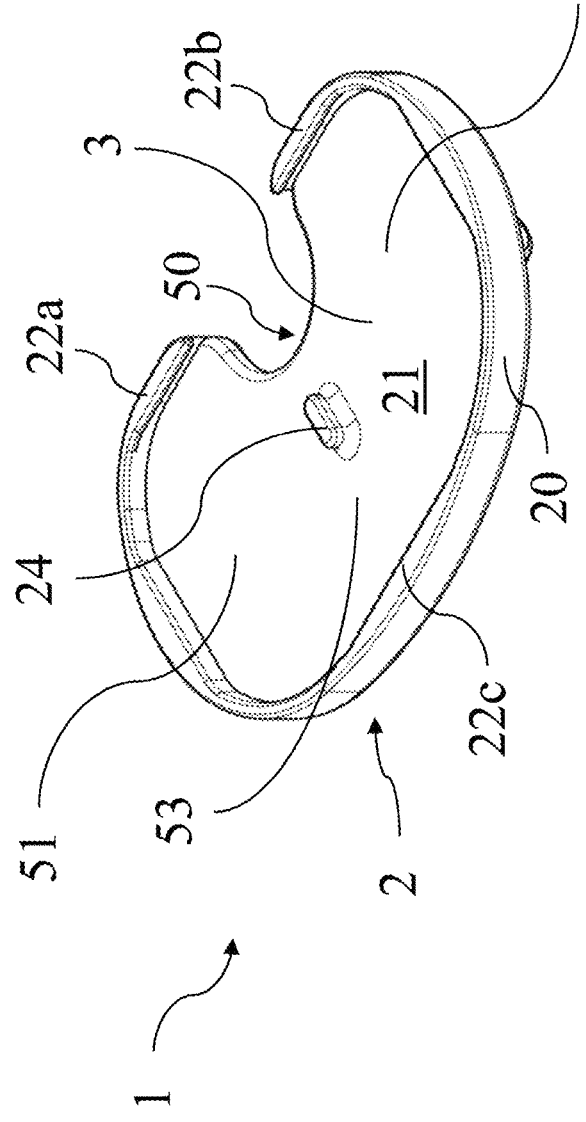
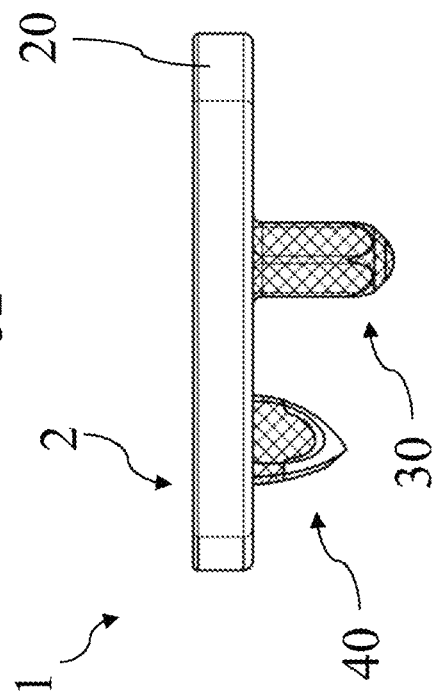
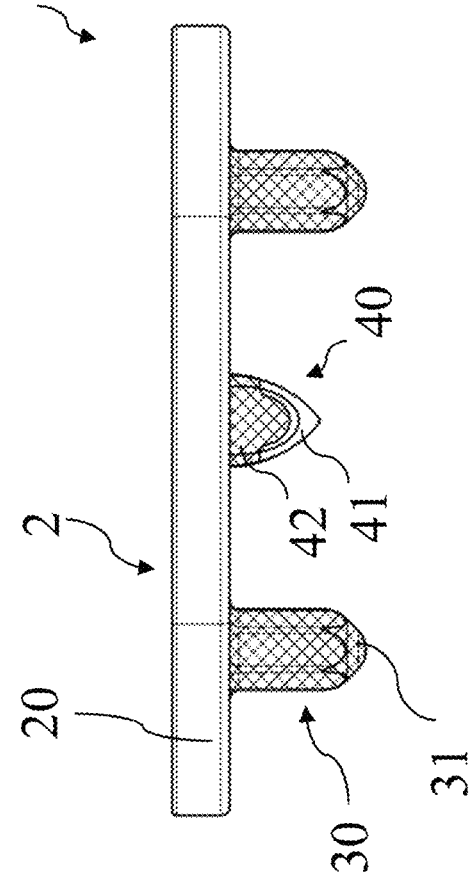

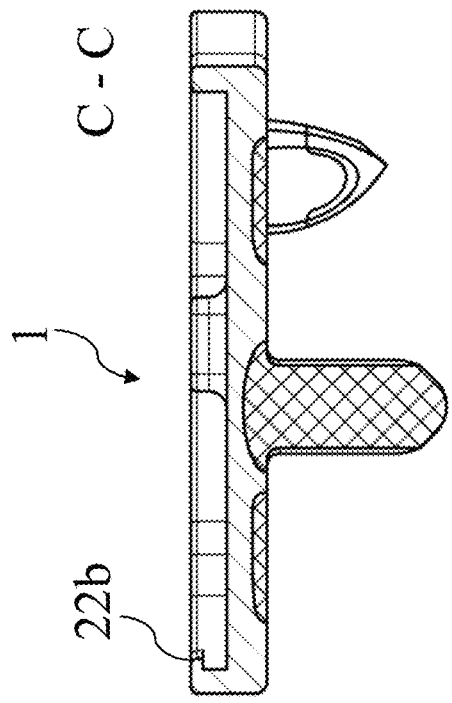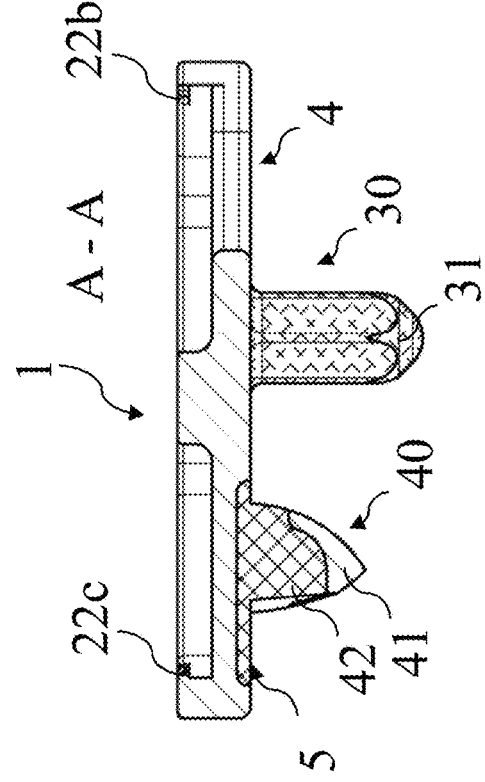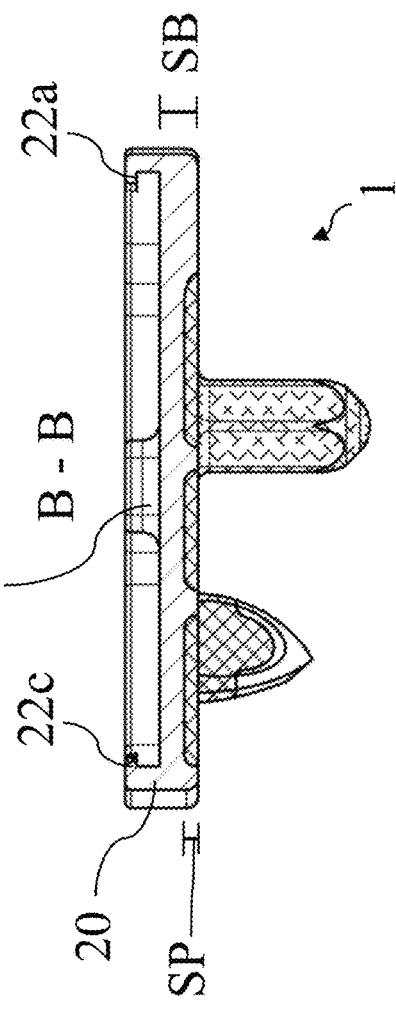

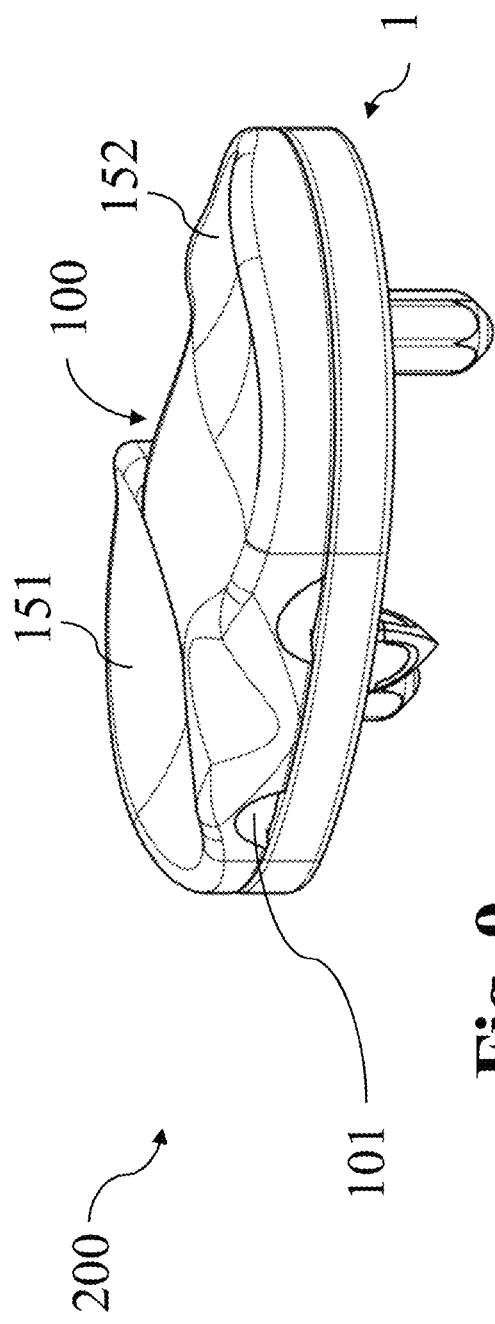
Fig. 9
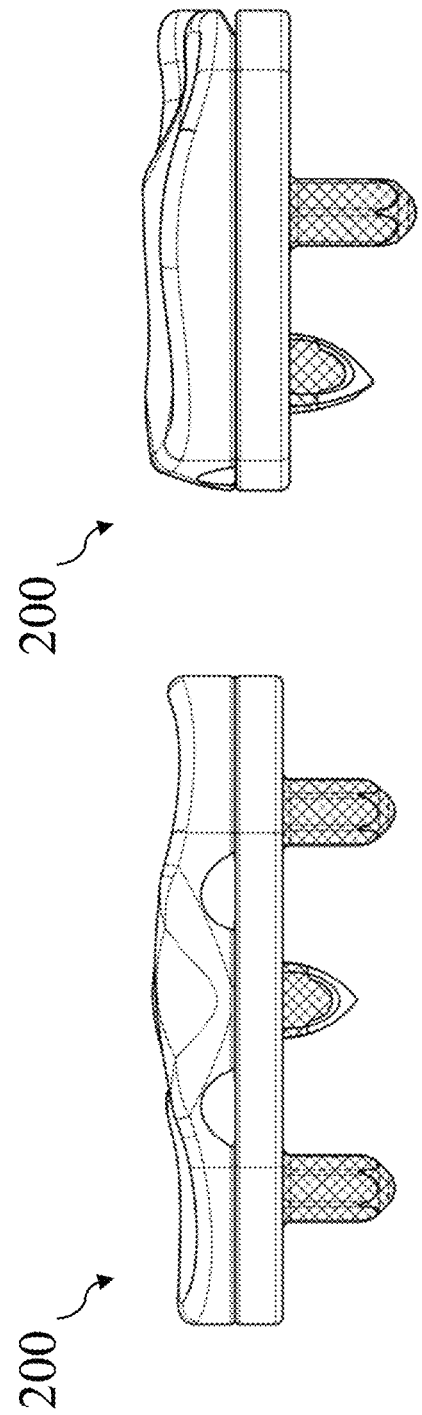
Fig. 10
Fig. 11

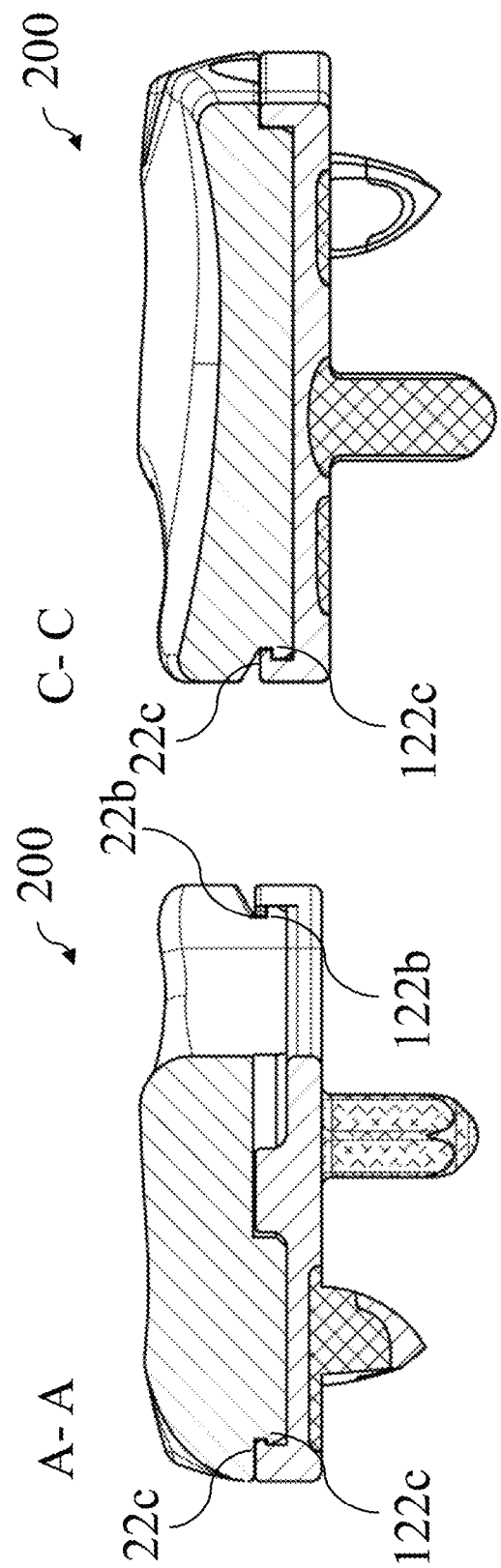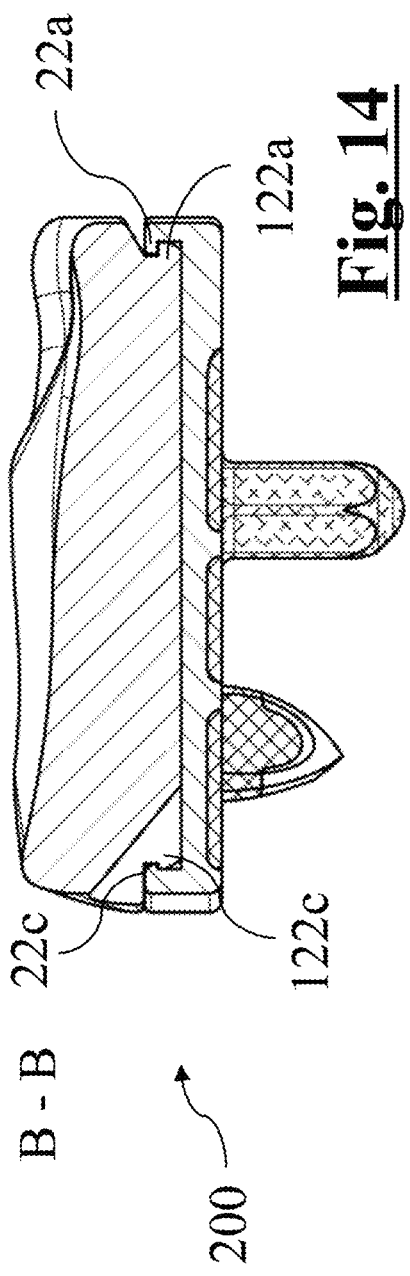

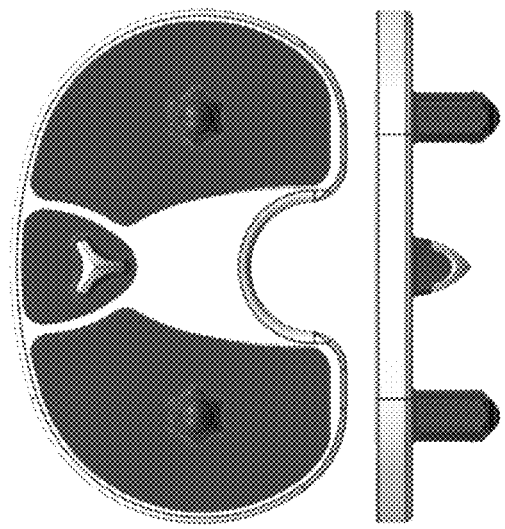
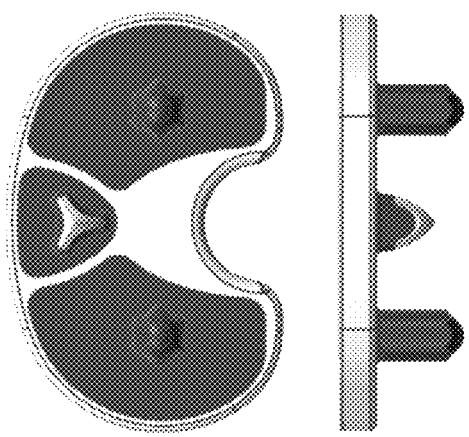
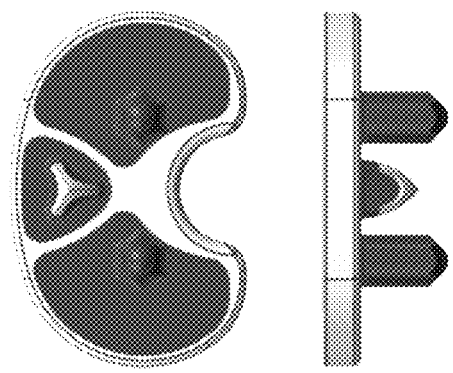
Fig. 19

B - B

A - A

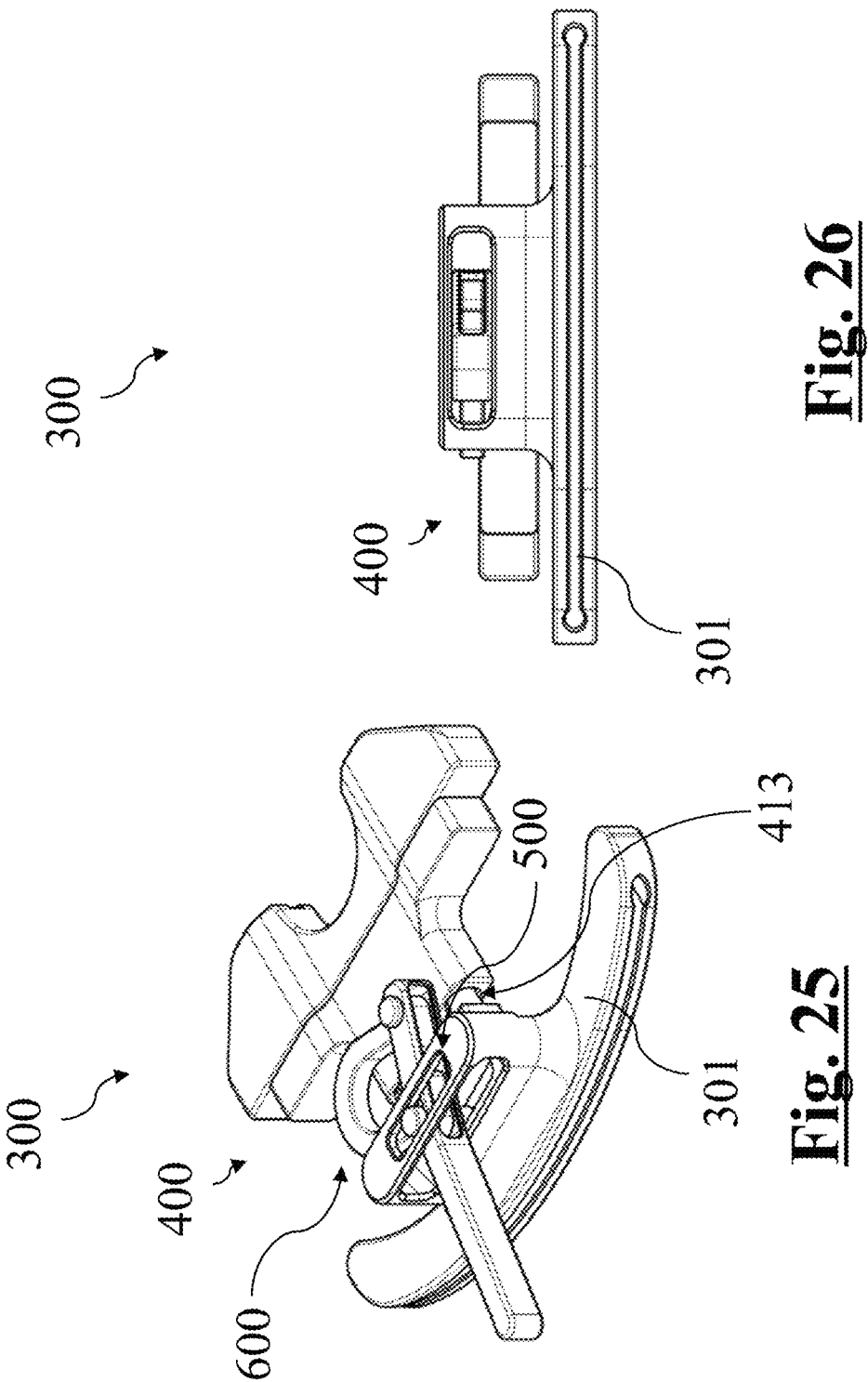

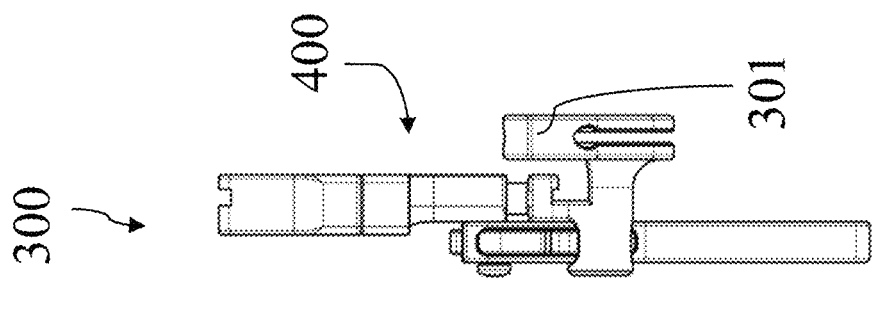
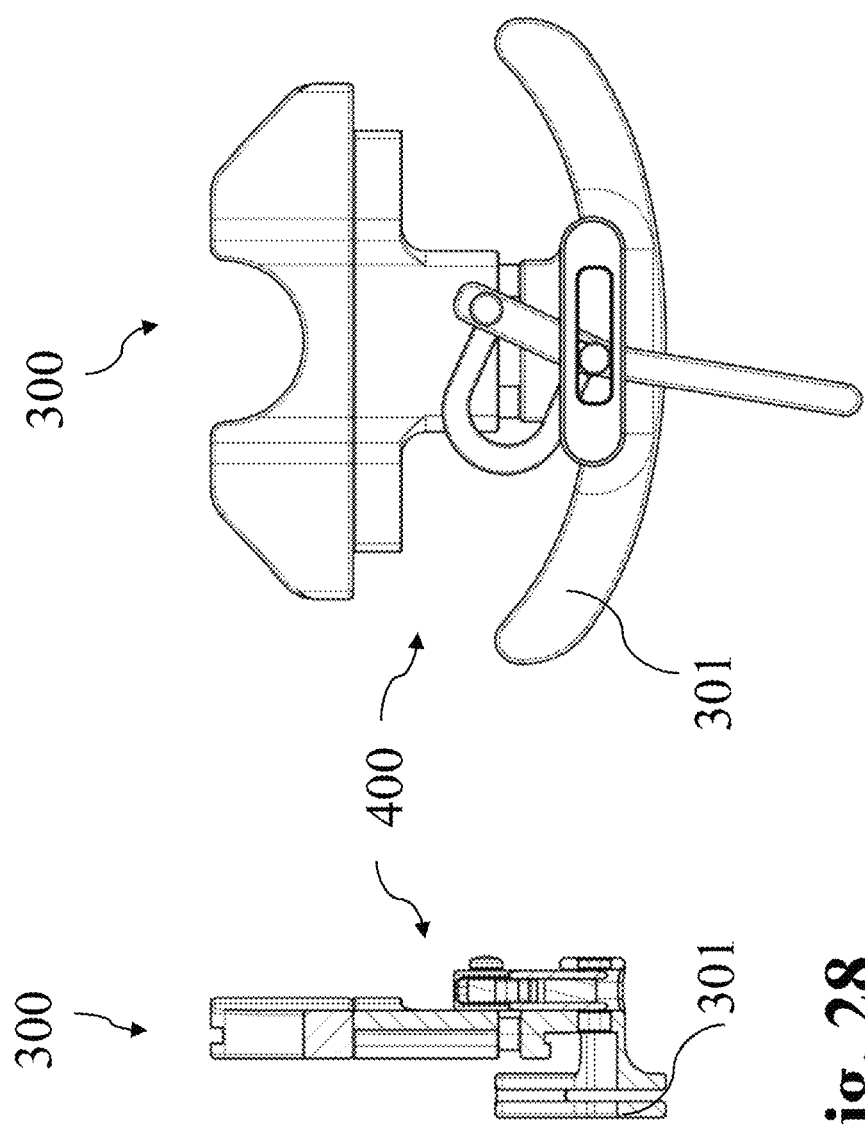
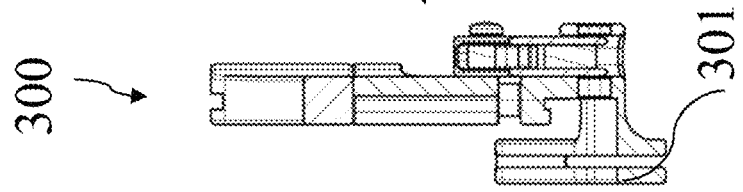

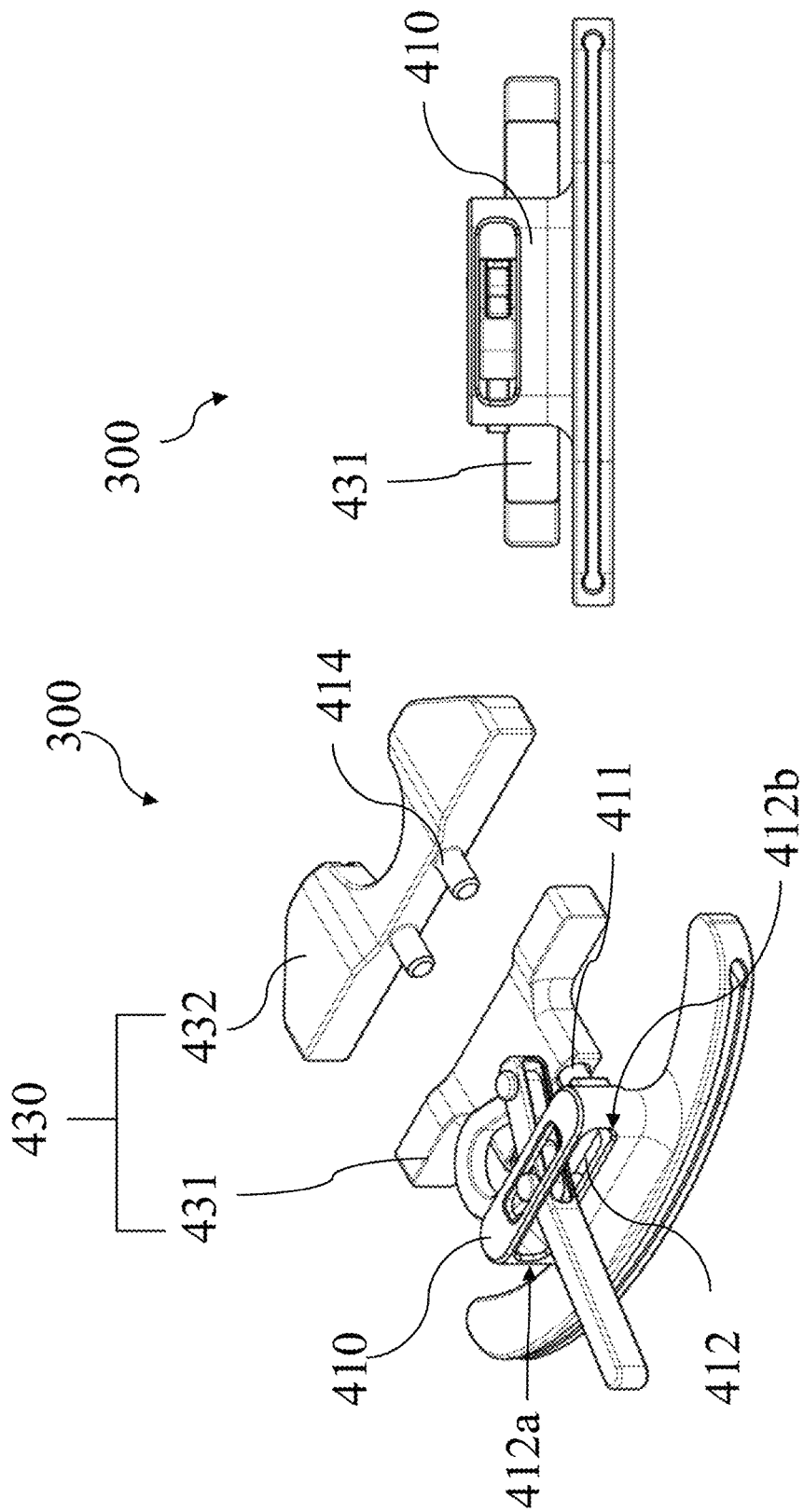

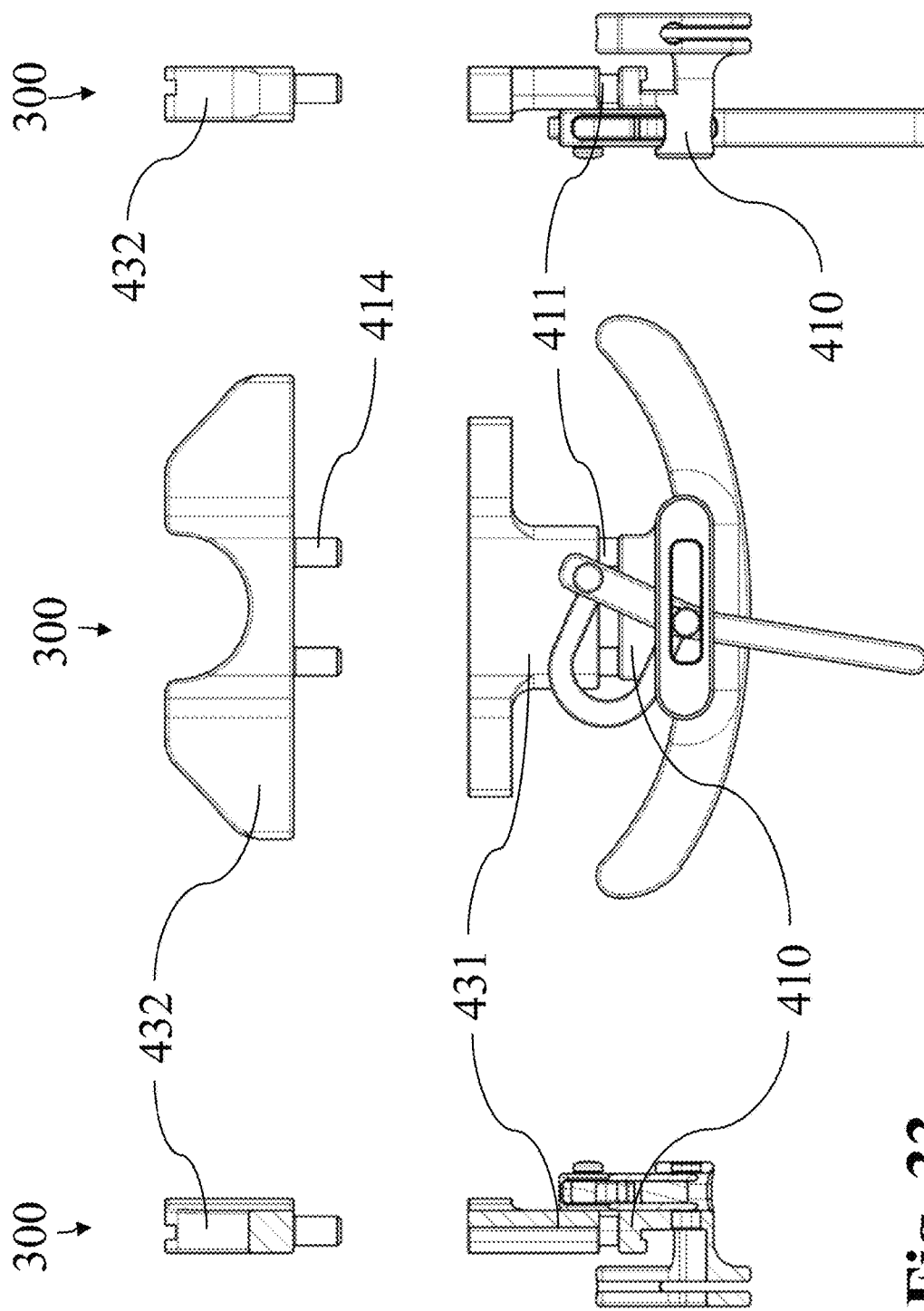

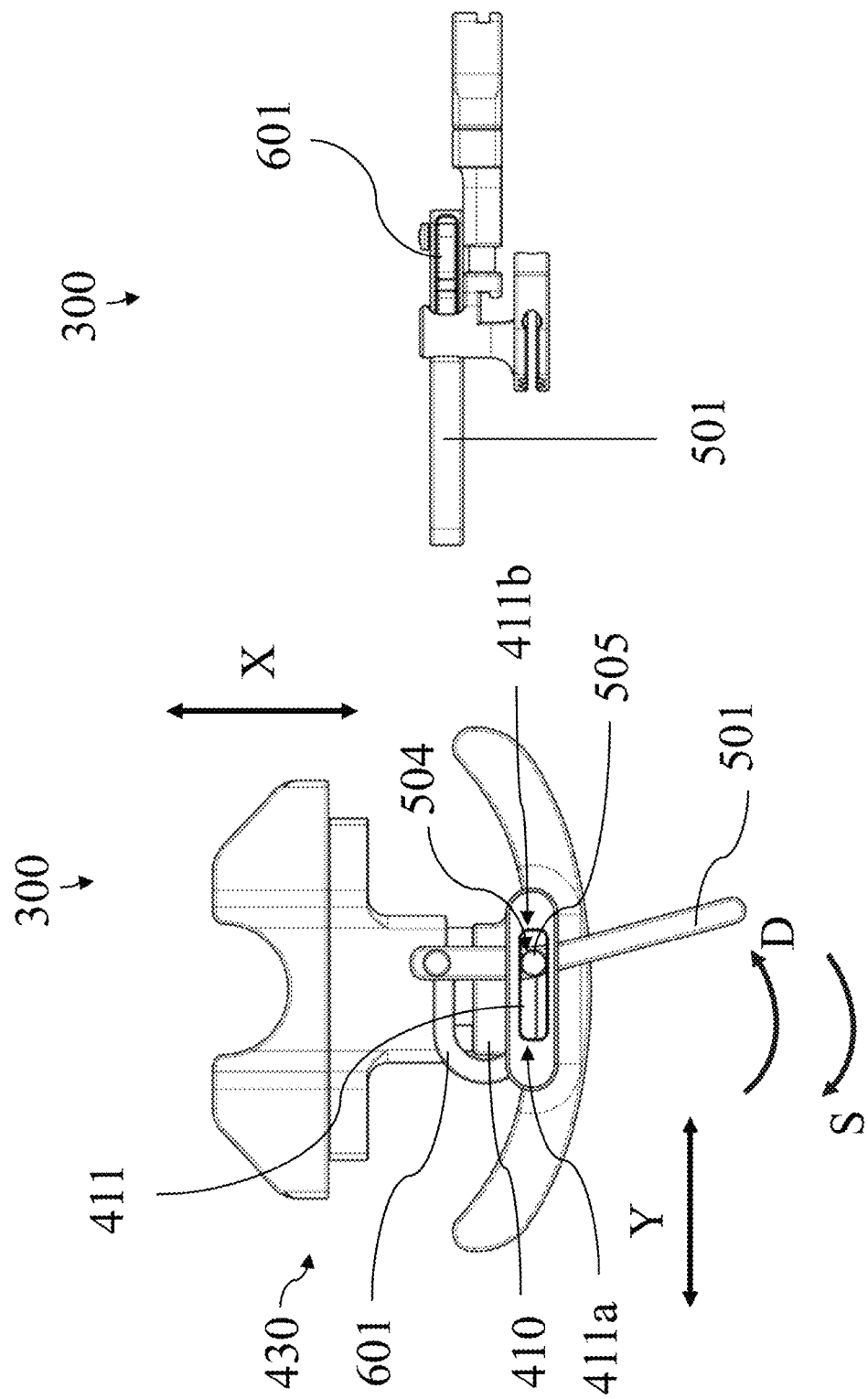

TIBIAL BASEPLATE FOR TIBIAL COMPONENT OF A KNEE PROSTHESIS, TIBIAL COMPONENT COMPRISING THE TIBIAL BASEPLATE AND METHOD FOR MANUFACTURING THE TIBIAL BASEPLATE

RELATED APPLICATIONS

The present application is a continuation application of Int. Pat. App. No. PCT/EP2020/054937, filed Feb. 25, 2020 and entitled "Tibial Baseplate for Tibial Component of a Knee Prosthesis, Tibial Component Including the Tibial Baseplate and Method for Manufacturing the Tibial Baseplate", which claims priority to EP Pat. App. No. 19160133.5 filed Feb. 28, 2019, and EP Pat. App. No. 19163638.0 filed Mar. 19, 2019, the entire disclosures of which are hereby incorporated herein by reference.

TECHNICAL FIELD

The present invention relates to a tibial baseplate for tibial component of a knee prosthesis. More particularly, a tibial baseplate of the type including at least a porous portion to allow bone ingrowth.

The tibial baseplate can be suitably used in a cementless tibial component of a knee prosthesis.

The invention also relates to a tibial component including the tibial baseplate and to a method for manufacturing the tibial baseplate.

The invention also relates to a kit including the tibial baseplate and an implant removal tool.

BACKGROUND

As it is known in this technical field, a total knee prosthesis includes normally two mutually articulating prosthesis components that replicate the kinematic of natural joint: a femoral component to be attached to a femur distal end and a tibial component to be attached to a tibia proximal end.

The tibial component, in turn, includes a metal baseplate attached to the tibial plateau previously transversally cut. On the top of the metal baseplate is usually fixed a polymeric liner that acts as a low wear bearing on which the femoral component articulates.

Depending on the type of the fixation to the bone, prosthesis used in this art are called cemented or cementless.

In cemented knee prosthesis, components are fixed to the bone by means of bone cement. On the contrary, cementless knee prosthesis are directly fixed to the bone.

To promote the osteointegration of the implant, a cementless baseplate is usually provided with a porous material to be placed in contact with the bone in order to allow bone ingrown. Stabilization elements to be inserted into the bone are also usually provided extending from a bone contacting surface of the baseplate.

More particularly, a monolithic tibial component includes a baseplate completely made in a porous material that is pasted or fused underneath a polymeric liner.

A cementless tibial component could also be modular. In this case, the tibial component is provided with a baseplate that allows to removably coupling the polymeric liner. In this way, the surgeon could choose from different heights to balance the knee joint and also substitute the liner in case of damages.

In this type of components, the baseplate includes to portions: a proximal solid portion having a proximal surface designed to accommodate the liner, and a distal porous portion having a distal surface to contact the tibial plateau. The porous portion is pasted or fused underneath the solid portion.

Though advantageous under various aspects and substantially responding to the purpose, the cementless tibial components of the prior art have a series of drawbacks, More particularly due to presence of an interface (paste or fused material) between the liner and the baseplate (modular tibial component) and between the solid and porous portions of the baseplate (prior art technology of adding in a second step the porous portion to the solid one).

Due to the cyclical loads, that the tibial component undergoes during the entire duration of the implant, the presence of an interface between the solid and the porous portion facilitates degradation phenomena such as delamination and galvanic effect. This degradation phenomena decreases the structural solidity and mechanical strength of the interface causing the implant failure.

More particularly, the phenomena can cause an incorrect load transfer to the bone, that promote a bone resorption determining at least a partially detachment of the implant.

The technical problem underlying the present invention is that of providing a baseplate having structural and functional features, that allow to overcome the drawbacks of prior art and more particularly having high structural solidity and mechanical resistance in addition to guarantee a proper fixation to the bone and implant stability during the whole duration of the implant.

Another aim of the present invention is to provide a tibial component including an innovative above-mentioned tibial baseplate and a method for manufacturing such a tibial baseplate.

SUMMARY

The technical problem previously identified is solved by a tibial baseplate for tibial component of a knee prosthesis including: a bulk solid portion including a proximally facing surface adapted to accommodate a bearing element for the articulation of a femoral component of the knee prosthesis; a plurality of porous portions integral with the bulk solid portion having a porous portion contacting surface opposite to the proximally facing surface adapted to contact a proximal tibia; where the plurality of porous portions are seamlessly incorporated in the bulk solid portion and are embedded into the bulk solid portion.

In other words, the tibial baseplate is a single element including a bulk portion of solid material and a plurality of portions in porous material that are integrated in the bulk portion with a seamlessy transition between porous and solid.

The absence of interfaces confers to the baseplate an increased structural solidity and adhesion resistance respects to tibial baseplates of prior art reducing the risk of delamination, shedding and galvanic effects typical of macro-rough coatings.

The tibial baseplate could be made in titanium or titanium alloy.

The tibial baseplate could be completely manufactured by means of additive manufacturing, such as for example Electron Beam Melting, even in a single step.

The additive manufacturing allows to build the whole tibial baseplate layer by layer. In this way, it is possible to produce tibial baseplates having complex structures, such as with porous portions incorporated into a solid bulk. Without separately producing solid and porous portions and then assembled them together as the baseplates of the prior art.

The porous portion can be created with a thickness between 0.8 and 1.2 mm, for example 1.2 mm allowing the porous structure to be completely interconnected, which provides an optimal basis for bone ingrowth.

The ratio between thickness of solid and porous phases is in this way optimized to guarantee a good bone ingrowth conditions and reducing micromotion when the baseplate is implanted.

The tibial baseplate includes a plurality of porous portions incorporated in the bulk solid portion, with porous portions separated from each other by part of the bulk solid portion. In other words, the porous portions are embedded into the bulk solid portion. The solid parts between porous portions act as reinforcement of entire structure increasing strength of the baseplate.

The tibial baseplate could include at least one stabilization element adapted to be inserted into the proximal tibia distally extending from a bone contact surface of the tibial baseplate opposite the proximal facing surface and adapted to be placed directly in contact with the bone tissue of a cut tibial plateau.

More particularly, the stabilization elements could extend from the plurality of porous portions.

The at least one stabilization element is partially or completely made in a porous material, for example the same of the porous portions, in order to further reduce micromotions and improve load transfer.

A porous stabilization element is easier to be cut respect to a solid one.

The at least one stabilization element could be located anteriorly the tibial baseplate to reduce micromotion and avoid lift off from the tibial baseplate due to a posterior or back load when it is implanted.

More particularly, a spike could be provided anteriorly. This spike having a substantially a pyramidal shape with a substantially triangular base with concave sides. This triangular base having at least one side that is longer than the others. More particularly, the pyramid's base could be substantially an equilateral triangle with its base located anteriorly respect the spike tip.

The at least one stabilization element could also include a base body made in a porous material and a tip made in a solid material; the solid material facilitates insertion into proximal tibia and limits the bone ingrowth at the tip making revision easier.

Tibial baseplate could include at least two stabilization elements located posteriorly with regards the frontal plane of the tibial baseplate. The tibial baseplate could have two posterior stabilization elements aligned in medio-lateral direction and separated by a linear distance that varies depending on the size of the tibial baseplate.

For example, the linear distance could be from 24.7 to 50.7 mm or from 40.95% to 61.6% of the tibial base plate size.

The posterior stabilization elements could be located at 55% of the antero-posterior width of the baseplate. This, positioning contributes to minimize micromotions while reducing the risk of penetrating the posterior cortex of the tibia. In alternative embodiments, the posterior stabilization elements could be not aligned.

The posterior stabilization elements could be completely made in a porous material.

The tibial baseplate could have a shape symmetrical respect to the central sagittal plane. An alternative embodiment could be asymmetrical respect of the central sagittal plane.

The plurality of porous portions could be distributed in a pattern that optimized bone integration and load transfer to the bone underneath the baseplate. The plurality of porous portions could define a pattern symmetrical respect to the central sagittal plane.

The technical problem is also solved by a method for manufacturing a tibial baseplate as discussed above including manufacturing the tibial baseplate layer by layer by additive manufacturing, such as for example EBM.

The technical problem is also solved by a tibial component for a knee prosthesis including the tibial baseplate as discussed above and a bearing element adapted to be accommodated on the proximally facing surface of the tibial baseplate.

The at least one stabilization element could be advantageously cut by means of an implant removal tool that includes a cutting guide adapted to guide a saw blade into the at least one stabilization element and an adapter holding the cutting guide adapted to lock the implant removal tool to the tibial baseplate; the adapter including a first adapter part and a second adapter part adapted to abut at a wall that surrounds the proximal facing surface of the tibial baseplate defining a seat when the adapter is inserted into the seat; where the first adapter part and the second adapter part are able to move away from each other in a direction parallel to the proximal facing surface abutting the first adapter part and the second adapter part at the wall locking the adapter to the tibial baseplate.

The second adapter part includes a second adapter part modular extension that is shaped to adapt the adapter to fit a seat of a tibial baseplate of a determinate size; the second adapter part modular extension being replaceable with another second adapter part modular extension adapted to a seat of tibial baseplate of different size.

Providing a plurality of second adapter part modular extensions, the implant removal tool could be adapted to tibial baseplates of different sizes, shapes and/or dimensions.

The adapter could also include adapter teeth designed to be inserted under respective teeth of the tibial baseplate to hold the adapter into the seat. Advantageously, the teeth of the tibial baseplate could be the same used to hold a bearing element into the seat.

In other words, the implant removal tool could be fixed to tibial baseplate using the same features used to accommodate the bearing element.

The cutting guide could have a substantially arched shape that follow a rounded profile of the tibial baseplate, More particularly an anterior profile of the tibial baseplate.

The implant removal tool could include a slide mechanism to reciprocally move the first and second adapter parts.

The slide mechanism could include a lever with a first lever end hinged to the second adapter part and anther point of the lever forced to translate respect to the first adapter part in a sliding direction orthogonal to the direction of motion of first and second adapter parts.

In this way, a rotation of the lever in a first rotation direction moves first and second adapter parts away from each other and a rotation of the lever in a second rotation direction opposite the first rotation direction approaches first and second adapter parts.

The implant removal tool could further include locking means for locking the lever when the first and second adapter parts are inserted into the seat of the tibial baseplate and maximally spaced each other abutting the wall surrounding the proximal facing surface of the tibial baseplate. In this way, implant removal tool is firmly locked into the tibial baseplate in order to withstand forces during the removal procedure and vibration of the saw blade during cutting of stabilization elements.

The locking means includes an elastic element integral with the lever.

The elastic element could be designed to be accommodated in a second slot of the first adapter part during lever rotation in the first rotation direction and being maximally compressed abutting a first second extremity of the second slot when the lever is completely rotated in a first rotation direction, and the first and second adapter parts are maximally spaced one with respect to the other.

Thus, the elastic element allows to maintain first and second adapter parts abutting the wall of the baseplate during the cutting of the stabilization pin.

The elastic element could have a substantially U-shape with a first elastic element end fixed at a first lever end and a second elastic element end fixed at a lever point between the first lever end and a second lever end.

Further features and advantages will become clearer from the following detailed description of exemplary, but not exclusive, embodiments of the present invention with reference to the attached figures that are given for instance and not limiting to it.

BRIEF DESCRIPTION OF THE DRAWINGS

FIG. 1 represents a distal perspective view of a first embodiment of the tibial baseplate according to the present invention;

FIG. 2 represents a posterior view of tibial baseplate of FIG. 1;

FIG. 3 represents a lateral view of tibial baseplate of FIG. 1;

FIG. 6 represents a cut sectional view A-A along the central sagittal plane of tibial baseplate of FIG. 5;

FIG. 7 represents a cut sectional view C-C parallel to the sagittal plane of tibial baseplate of FIG. 5 through the center of the stabilization peg;

FIG. 8 represents a transversal sectional view B-B along parallel to the sagittal plane of tibial baseplate of FIG. 6;

FIG. 9 represents a distal perspective view of a tibial component according to the present invention;

FIG. 10 represents a frontal view from anterior of tibial component of FIG. 9;

FIG. 11 represents a lateral view of tibial component of FIG. 9;

FIG. 12 represents a cut sectional view A-A along the central sagittal plane of tibial component of FIG. 9;

FIG. 13 represents a cut sectional view C-C parallel to the sagittal plane of tibial component of FIG. 9;

FIG. 14 represents a transversal sectional view B-B parallel to the sagittal plane of tibial component of FIG. 9;

FIG. 19 represents a proximal views and related posterior views of tibial baseplate of FIG. 15 with three examples of different sizes;

FIG. 25 represents a prospective view of implant removal tool for cutting stabilization elements of the tibial baseplate of FIG. 1;

FIG. 26 represents an anterior view of the implant removal tool of FIG. 25;

FIG. 27 represents a top view of the implant removal tool of FIG. 25;

FIG. 28 represents a sectional view of the implant removal tool along the central sagittal plane of FIG. 25;

FIG. 29 represents a lateral view of the implant removal tool of FIG. 25;

FIG. 30 represents a prospective view of implant removal tool of figure with second adapter part disassembled;

FIG. 31 represents an anterior view of the implant removal tool of FIG. 30;

FIG. 32 represents a top view of the implant removal tool of FIG. 30;

FIG. 33 represents a sectional view of the implant removal tool of FIG. 30;

FIG. 34 represents a lateral view of the implant removal tool of FIG. 30;

FIG. 42 represent a prospective view of the implant removal tool of figure in an extended configuration;

FIG. 43 represent a lateral view of the implant removal tool of FIG. 42;

DETAILED DESCRIPTION

Figure 5:
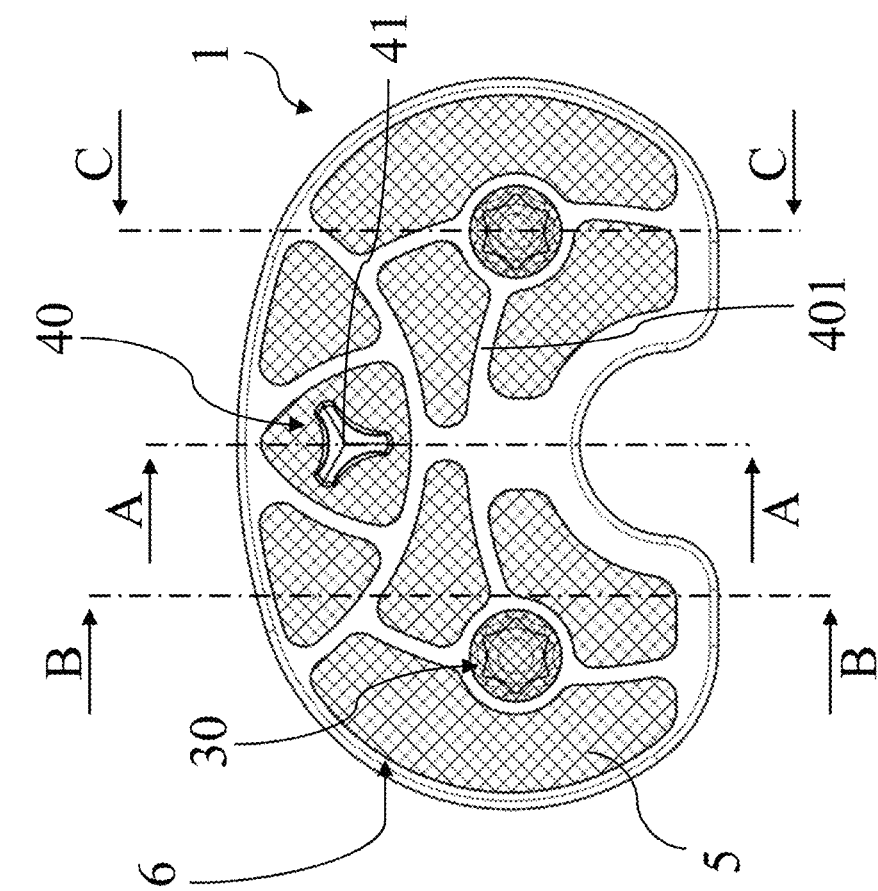
FIG. 5 represents a proximal view of tibial baseplate of FIG. 1.

With reference to the attached figures, exemplary embodiments of tibial baseplate according to the present invention is generally identified by 1, 1' and 1".

Terms "proximal", "distal", "superior", "inferior", "medial", "lateral" used in the description refer to the position of the tibial baseplate when implanted on the proximal tibial in a known manner. More particularly, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

Further, planes are defined in the know matter: frontal plane, perpendicular to the anterior-posterior direction, sagittal plane, perpendicular to the medio-lateral direction and transverse plane, perpendicular to the proximal-distal direction. A central sagittal plane is defined as parallel to the sagittal plane passing through the center of the line, which connects the most lateral point with the most medial point of the tibial plate (medio-lateral center of the tibial plate).

The tibial baseplate 1, 1', 1" is specifically adapted for use in a cementless modular tibial component 200 of a knee prosthesis.

The tibial baseplate 1 is designed to replace the proximal part of the tibia and to be implanted directly onto the tibial plateau previously transversally cut and proximally accommodate a bearing element 100, such as a polymeric liner, on which the femoral component of the knee prosthesis articulates.

The tibial baseplate 1 includes a bulk solid portion 2 having a shape symmetrical respect to the central sagittal plane of symmetry. The external profile in the transverse plane of the bulk solid portion 2 has substantially a kidney-shape and approximates external transversal perimeter of the cut tibial plateau, with a recess 50 located in a central posterior location between a first condylar region 51 and a second condylar region 52 to accommodate the posterior cruciate ligament.

Alternative embodiments of the tibial baseplate could have an asymmetrical shape with respect to the central sagittal plane. See for example tibial baseplate 1" shown in FIGS. 20-24. The bulk solid portion is made in a solid material and is proximally delimited by a proximally facing surface 3 on which the bearing element 100 could be placed.

The bulk solid portion is made of a single material, More particularly titanium or titanium alloy.

As shown in FIG. 1, the proximally facing surface 3, with exception of the recess 50, is delimited by a perimetric wall 20 extending in proximal direction. This perimetric wall 20 defines a seat 21 for accommodating the bearing element 100. The wall 20 concurs to lock the bearing element onto the proximally facing surface 3. Alternative embodiments could be provided with other types of locking mechanisms.

From a central region 53 of the proximally facing surface 3 a positioning island 24 for guiding the insertion of the bearing element 100 into the seat 21 extends. In alternative embodiments the island 24 could not be present.

The perimetric wall 20 is provided with holding means for holding the bearing element 100 into the seat 21.

More particularly, the holding means include a first posterior tooth 22a extending anteriorly from the top of the wall 20 where that wall 20 posteriorly delimits the first condylar region 51 and a second posterior tooth 22b extending anteriorly from the top of the wall 20 where that wall 20 posteriorly delimits the second conciliar region 52. The holding means include also an anterior tooth 22c extending posteriorly from the top of the anterior-central part of the wall 20.

FIGS. 6-8 show different transversal sections of the tibial baseplate 1 where are visible the holding means 22a, 22b, 22c.

FIGS. 12-14 show transversal sections of FIGS. 6-8 where the bearing element 100 is snap fit into the seat 21 of the tibial baseplate 1 and hold by mean of the holding means 22a, 22b, 22c. As can be seen in these figures the bearing element 100 is provided with conjugated bearing element teeth 122a, 122b, 122c design to be inserted beneath corresponding teeth 22a, 22b, 22c of the tibial baseplate 1 to hold the bearing element 100 into the seat 21.

The bearing element 100 is shaped with concave surfaces 151, 152 in correspondence of the condylar regions 51, 52 in order to fit the convex surfaces of artificial condyles of the femur component, in a known manner. Other shapes of the bearing element surfaces could be provided.

As shown in FIGS. 9 and 10, the bearing element 100 is also frontally provided with two tabs 101 suitable for removing the bearing element 100 from the seat 21.

Figure 4:
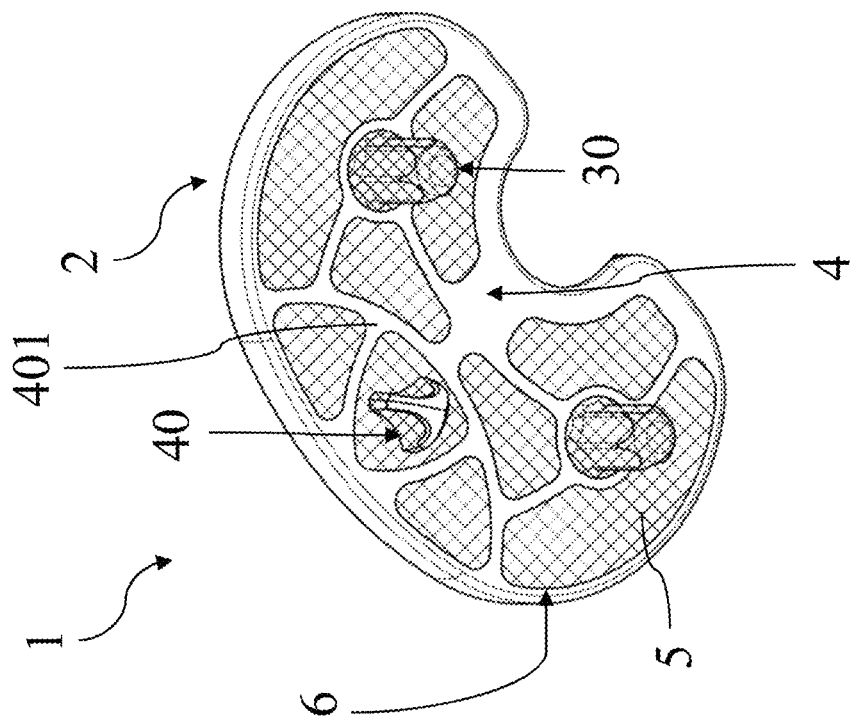
FIG. 4 represents a proximal perspective view of tibial baseplate of FIG. 1.
Figure 16:
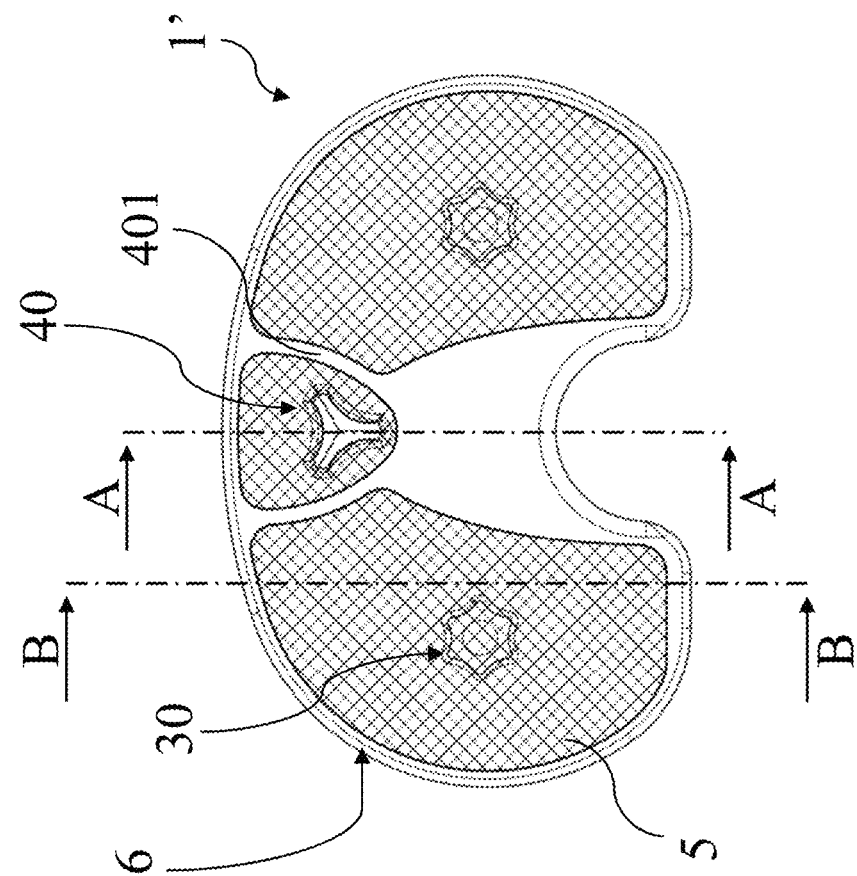
FIG. 16 represents a proximal view of tibial baseplate of FIG. 15.
Figure 15:
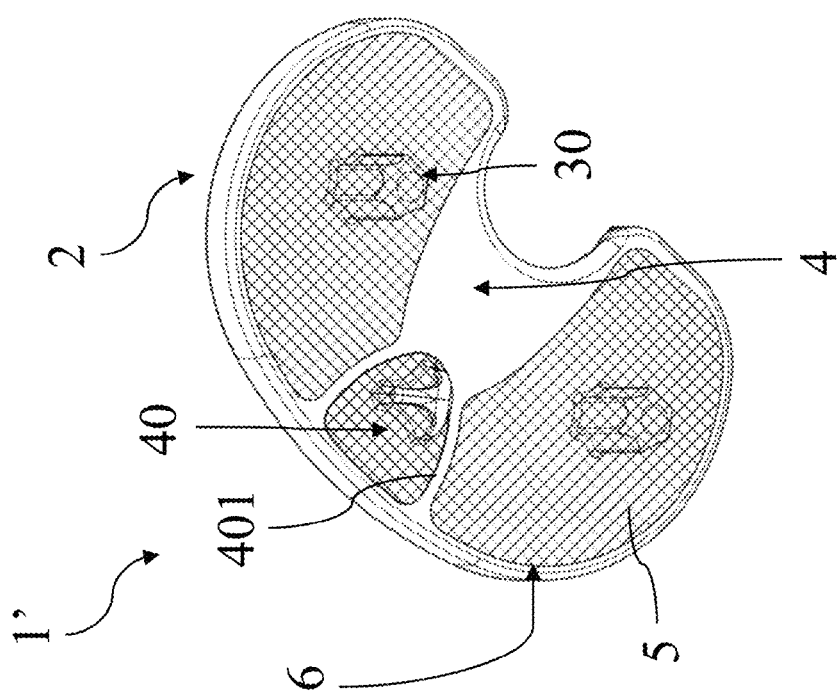
FIG. 15 represents a proximal perspective view of a second embodiment of the tibial baseplate according to the present invention.
Figure 17:
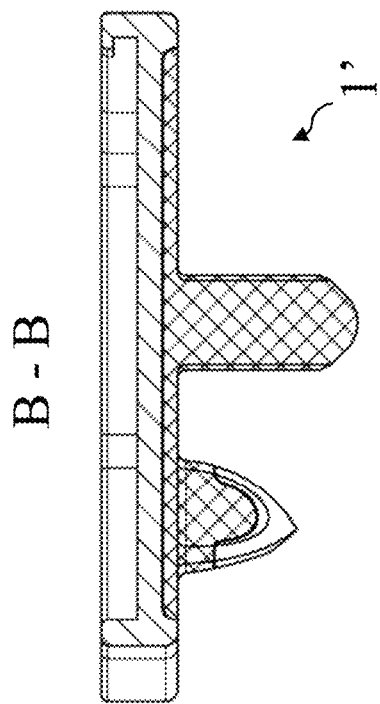
FIG. 17 represents a cut sectional view A-A along the central sagittal plane of tibial baseplate of FIG. 16.
Figure 18:
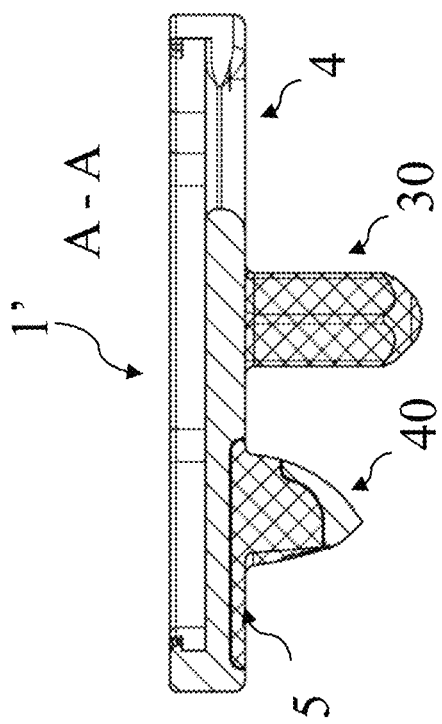
FIG. 18 represents a cut sectional view B-B parallel to the sagittal plane of tibial baseplate passing through the center of the stabilization element of FIG. 16.
Figure 21:
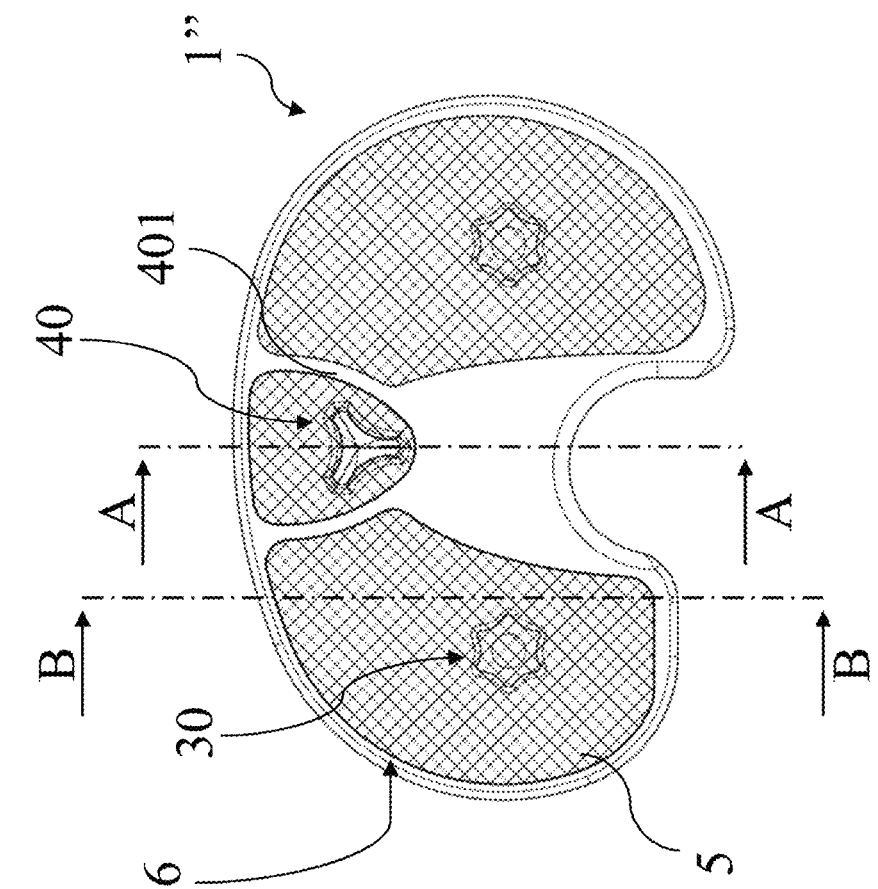
FIG. 21 represents a proximal view of tibial baseplate of FIG. 20.
Figure 20:
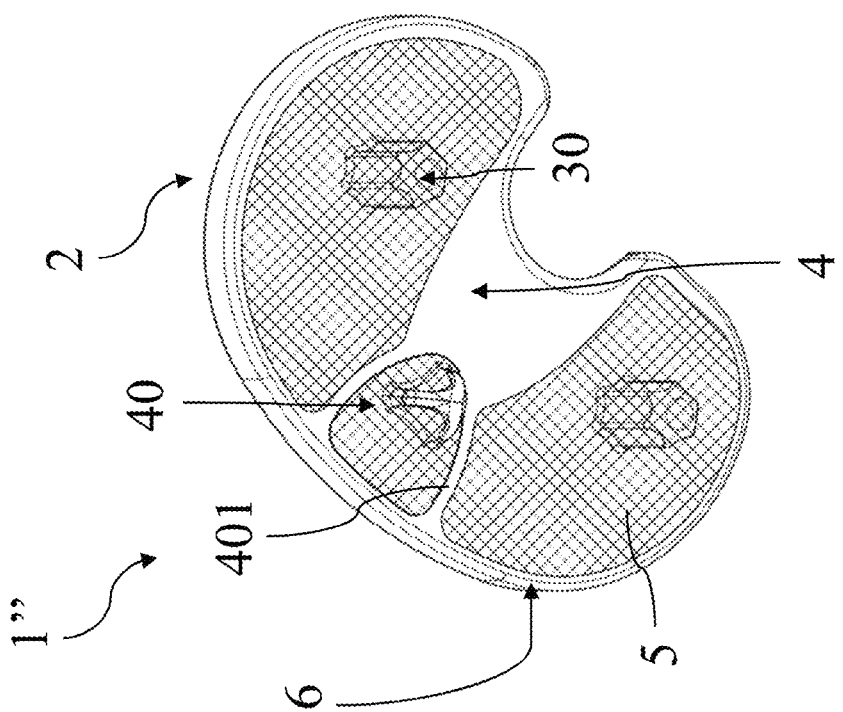
FIG. 20 represents a proximal perspective view of a third embodiment of the tibial baseplate according to the present invention.
Figure 22:
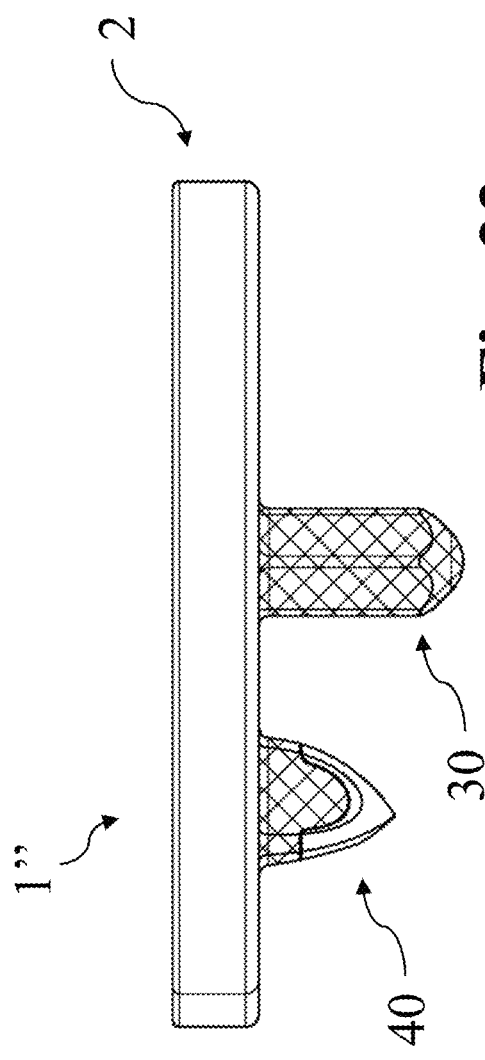
FIG. 22 represents a lateral view of tibial baseplate of FIG. 20.
Figure 24:
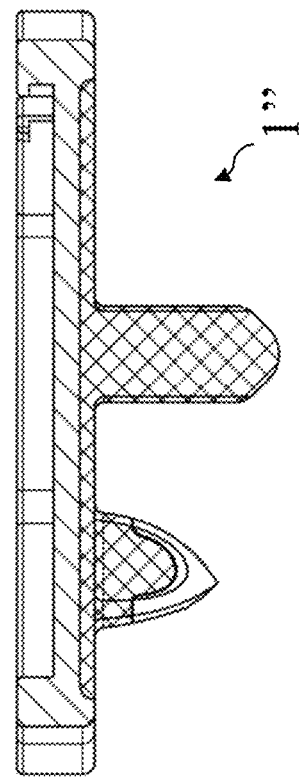
FIG. 24 represents a cut sectional view B-B parallel to the sagittal plane of tibial baseplate passing through the stabilization element of FIG. 21.
Figure 23:
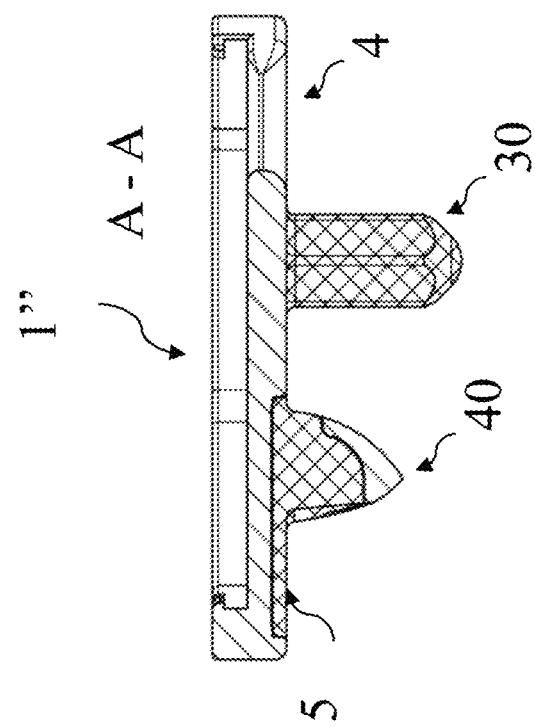
FIG. 23 represents a cut sectional view A-A along the central sagittal plane of tibial baseplate of FIG. 21.
Figure 36:
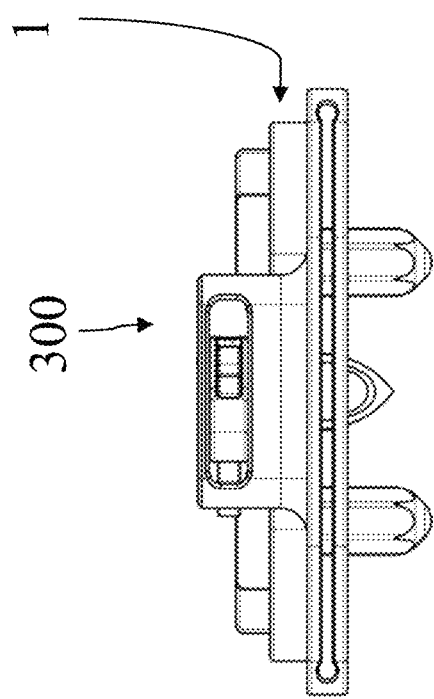
FIG. 36 represents an anterior view of the assembly of FIG. 35.
Figure 35:
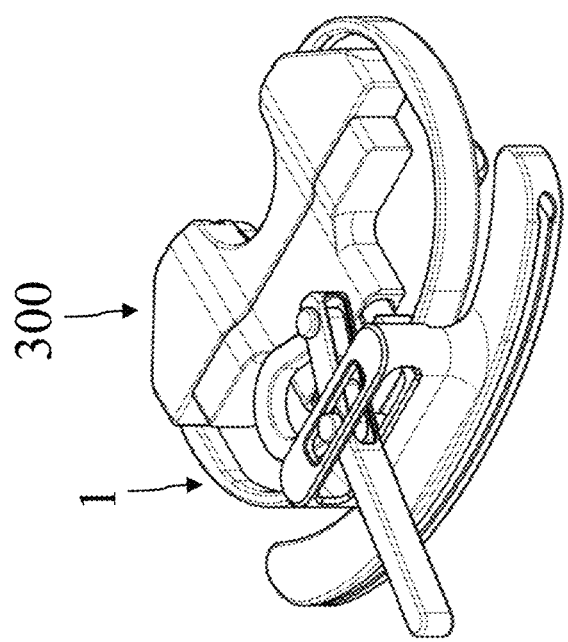
FIG. 35 represents a prospective view of the assembly including an implant removal tool of FIG. 35 mounted on the tibial baseplate of FIG. 1.
Figure 39:
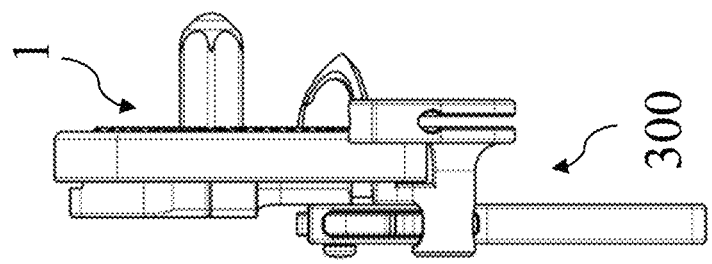
FIG. 39 represents a lateral view of the assembly of FIG. 35.
Figure 37:
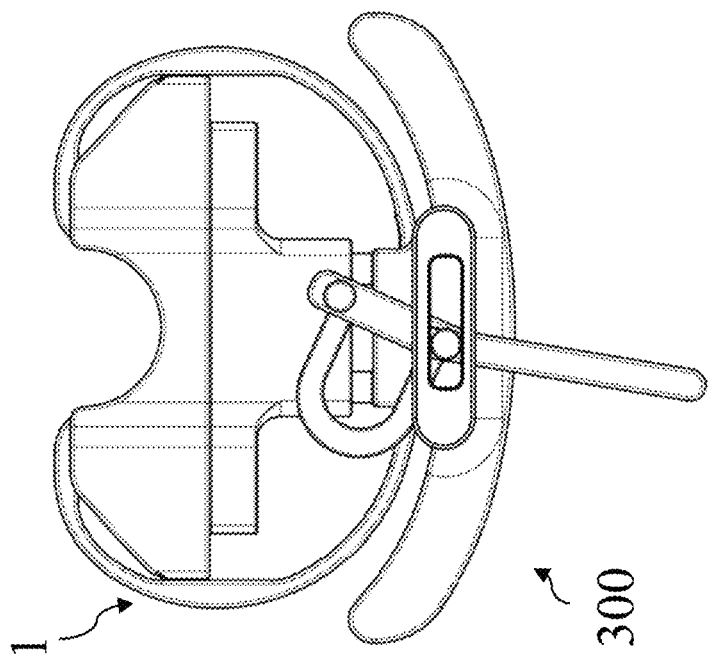
FIG. 37 represents a top view of the assembly of FIG. 35.
Figure 38:
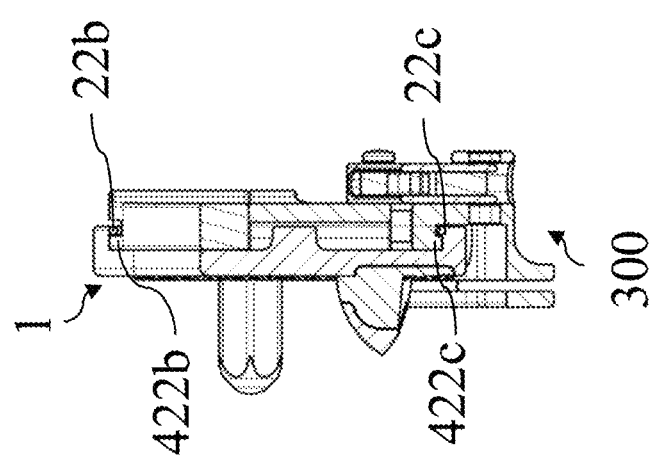
FIG. 38 represents a sectional view of the assembly of FIG. 35.

FIGS. 4 and 5 show a bone contact surface 4 of the tibial baseplate 1 opposite the proximal facing surface 3 adapted to be placed directly in contact with the bone tissue of a cut tibial plateau.

In the bulk solid portion 2 of the tibial baseplate 1 are seamless incorporated a plurality of porous portions 5 that extends from a porous portion contact surface 6 at the bone contact surface 4 into the bulk solid portion 2.

The porous portions are made of a single material, more particularly the same of the bulk solid portion.

The presence of porous portions 5 reduces the whole stiffness of the tibial baseplate. The stiffness and elasticity of the baseplate may depend, but not necessarily, on the porous portions thickness SP with respect to the bulk solid portion thickness SB and on number, dimension and distribution of porous portions 5.

In one embodiment of the present invention, the porous portions thickness SP substantially half than the bulk solid portion thickness SB (calculated excluding wall 20 and jap 24, see for instance the example of FIG. 8). For example, bulk solid portion thickness SB is 2 mm and porous portions thickness SP is 1.2.

As shown in FIGS. 4 and 5, the porous portions 5 are distributed in a pattern that is symmetrical respect to the central sagittal plane and separated one to each other by solid material of the bulk solid portion 2.

The plurality of porous portions 5 are in particular separated from each other by a solid part 401 of the bulk solid portion 2.

In other words, each porous portion is surrounded by solid material of the bulk solid portion except for the porous portion contact surface 6 that is adapted to contact the bone tissue.

Each porous portion 5 consists of a regular three-dimensional hexagonal cell structure with high open interconnected porosity that imitates the morphology of the trabecular bone.

High open porosity and adequate pore size enhance cell migration and vascularization, facilitating the transport of oxygen, nutrients, ions and bone inducing factors, favoring new bone formation. In other words, porosity promotes bone ingrowth or osteointegration indicating a successful combination of osteoconduction and osteoinduction.

Porous portion contact surfaces 6 of porous portions 5 are areas with higher coefficient of friction due to the roughness of porous structure.

Contact between the porous portion contact surface 6 enhances primary stability of the implant reducing micromotions. Together with the reduced effect of stress shielding due to the adaptation of the stiffness of the baseplate to physiological loading encourages biological fixation (secondary stability), bone-implant mechanical interlocking.

Alternative embodiments of the tibial baseplate could have different symmetrical patterns of the porous portions 5. More particularly, this embodiment avoids putting porous portions in a central region of the plate to improve its strength. See for example tibial baseplate 1' shown in FIGS. 15-18.

The tibial baseplate 1 includes also stabilization elements 30, 31 that extends distally from the bone contact surface 4 and are adapted to be inserted into the bone.

The tibial baseplate 1, 1', 1" according the embodiments here disclosed is provided with two types of stabilization elements 30, 40 having different shape: —a peg 30 with a rounded tip 31 and a transversal section with a profile shaped substantially as a six-point star; in other words, the peg 30 is an elongated pin having a hexagonal transversal section with concave sides.

a spike 40 with a tip 41 sharped.

The spike 40 has substantially a pyramidal shape with a substantially triangular base with concave sides. This triangular base has at least one side that is longer than the others. More particularly, as could be seen for example in FIG. 5, the pyramid's base is substantially an equilateral triangle with its base located anteriorly respect the tip 41.

More particularly, the tibial baseplate 1 is provided with two pegs 30 located in positions symmetric respect to central sagittal plane of symmetry of the tibial baseplate 1, one in correspondence of the first condylar region 51 and one in correspondence of the second condylar region 52.

Furthermore, pegs 30 are closer to the posterior side of the baseplate.

Each peg 30 is made of a porous material for example the same of the porous portions 5 and extends from a porous portion 5. Thus, the peg 30 is a projection of a porous portion 5 that extend distally from a porous portion contact surface 6.

Pegs 30 are aligned in a medio-lateral direction. The linear distance between the pegs 30 could vary depending of the size of the tibial baseplate.

FIG. 19 show examples of three size of the tibial baseplate 1" with different distances between pegs 30. This could be also applied to other embodiments of the tibial baseplate.

The spike 40 is instead located in a central and anterior position and its shape is symmetrical respect to the central sagittal plane of symmetry of the tibial baseplate 1.

Even the spike 40 extends from a porous portion 5 with a base body 42 made in a porous material as the porous portion and the tip 41 made in a solid material as the bulk solid portion. The tip 41 is seamlessly integral with the body base 42.

The tibial baseplate 1 according the embodiment here disclosed is made of one material, More particularly titanium or titanium alloy.

Here below it is described a favorite embodiment of an implant removal tool suitable for removing the tibial baseplate 1, for example during revision surgery, cutting the stabilization elements 30, 40 extending distally from the bone contact surface 4 of the tibial baseplate 1.

In FIGS. 25-45 the implant removal tool is generally identified by 300.

The implant removal tool 300 including an adapter 400 that is designed to be hold in the seat 21 of the tibial baseplate 1 abutting against the wall 20 that surrounds the proximal facing surface 3.

More particularly, the adapter 400 includes conjugated adapter teeth 422a, 422b, 422c designed to be inserted underneath respective teeth 22a, 22b, 22c of the tibial baseplate 1 to hold the adapter 400 into the seat 21, as discussed below.

The adapter 400 includes a first adapter part 410 and a second adapter part 430.

The first adapter part 410 supports a cutting guide 301 of the implant removal tool 300 that is integral with the first adapter part 410.

The second adapter part 430 is slidely coupling with the first adapter part 410 allowing a relative translation between the first and the second adapter part in a sliding direction X parallel to the proximal facing surface of the tibial baseplate 3 when the adapter 400 is inserted into the seat 21.

Two pins 411 protrudes from the first adapter part 410 and are slidely inserted into respective holes 413 of the second adapter part 430 guiding the relative translation of the first and second adapter parts.

The second adapter part 430 in turn includes a second adapter part main element 431 and a second adapter part modular extension 432 removably coupled. More particularly, second adapter part main element 431 is provided with the holes 413 and is relatively movable respect to the first adapter part 410; the second adapter part modular extension is coupled to second adapter part main element 431 and is specifically shaped to abut against the wall 20 of the tibial baseplate 1.

Advantageously, the second adapter part modular extension 432 could be provided in different sizes each for each size of tibial baseplate 1. In the present embodiment, the second adapter part modular extension 432 is coupled to the second adapter part main element 431 by means of pins 414

The above-mentioned cutting guide 301 is suitable for guiding a saw blade just below the bone contact surface 4 of the tibial baseplate 1 to cut the attachment elements 30, 40 when the adapter 400 is inserted into the seat 21. A cutting guide opening is indeed located on a plane just beneath the adapter 400.

The cutting guide 301 has a substantially arched shape that follow the rounded profile of the tibial baseplate 1, More particularly the anterior profile of the tibial baseplate 1.

The relative motion of first adapter part 410 and second adapter part 430 is actuated by means a slide mechanism 500.

The slide mechanism 500 includes a lever 501 having a first lever end hinged to the second adapter part main element 431 and a second lever end 503 opposite the first lever end 502 free to be pushed in order to rotate the lever 501.

A point 504 of the lever 501 located between first and second lever ends 502, 503 is coupled to the first adapter part 410 in a manner that restricted this point 504 to translate respect to the first adapter part 410 in a direction Y orthogonal to the sliding direction X and parallel to the plane of sliding of adapter parts 410, 430. More particularly, at the point 504 there is a slider 505 integral with the lever that slides into a first slot of the first adapter part 410 extending between a first slot extremity 411a and a second first slot extremity 411b.

A rotation of the lever 501 in a first rotation direction D moves first and second adapter parts 410, 430 away from each other and a rotation of the lever 501 in a second rotation direction S opposite the first rotation direction D approaches first and second adapter parts 410, 430 (see FIG. 42). Rotation of the lever 501 in first rotation direction D is stopped when slider 505 abut at second first slot extremity 411b and rotation of the lever 501 in second rotation direction S is stopped when slider 505 abut at first slot extremity 411a.

During its rotation the lever 501 is also inserted into a second slot 412 extending in the sliding direction X on a plane orthogonal to the plane of sliding of adapter parts 410, 430 from a first second slot extremity 412a and a second second slot extremity 412b.

The implant removal tool 300 further includes locking means 600 for locking the lever 501 when the first and second adapter parts 410, 430 are maximally spaced each other.

The locking means 600 includes an elastic element 601 fixed to the lever 501. As shown for example in FIG. 27, the elastic element 601 has a substantially U-shape with a first elastic element end 601a fixed at first lever end 502 and a second elastic element end 601b fixed at second lever end 503. The elastic element 601 is dimensioned to be accommodated in the second slot 412 during lever rotation in first rotation direction D and maximally compressed into the second slot 412 when lever 501 is completely rotated in first rotation direction D, the slider 505 abuts second first slot extremity 411b and the first and second adapter parts 410, 430 are maximally spaced each other.

With references to FIGS. 40-45 here below the operation of the tool 300 during a complete rotation in first rotation direction D is described.

Figures 40, 41:
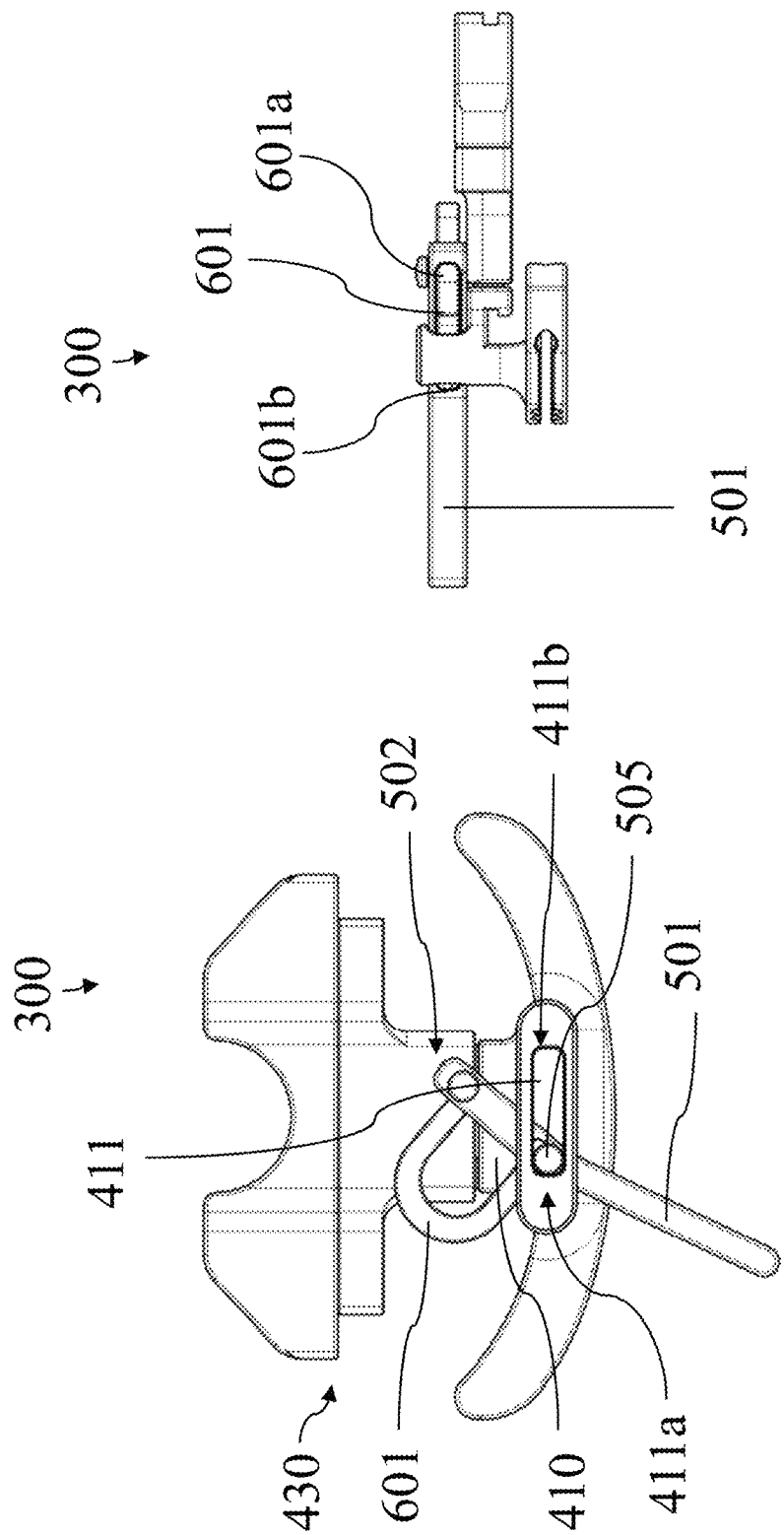
FIG. 40 represent a prospective view of the implant removal tool of figure in a closed configuration.
FIG. 41 represent a lateral view of the implant removal tool of FIG. 40.

In FIGS. 40 and 41 show tool 300 in a closed configuration with first and second adapter parts 410, 430 contacting each other, lever 501 comply rotated in second rotation direction S with the slider 505 abutting at first slot extremity 411a and elastic element 601 mostly out of the second slot 412.

Rotating the lever 501 in first rotation direction D, first and second adapter parts 410, 430 move gradually away from each other while the slider 505 slides into the first slot 411 and the elastic element 601 entering the second slot 412.

FIGS. 42 and 43 show tool 300 in an extended configuration with first and second adapter parts 410, 430 maximally spaced each other and elastic element 601 uncompressed and partially inside the second slot 412.

Starting with the tool 300 in a closed configuration it is inserted into seat of the tibial baseplate 1 posteriorly abutting the second adapter part 430 of the adapter 400 at the wall 20 of the tibial baseplate 1 inserting posterior adapter teeth 322a, 322b underneath corresponding teeth 22a, 22b of the tibial baseplate 1, as shown in FIGS. 37-41. If the removal guide 300 would be inserted into the tibial plate, this extension of the first and second adapter parts 410 and 430 would be limited due to the contact with the walls 22 of the tibial plate. This limitation would compress the elastic element 601. This situation corresponds to the maximum compression of the elastic element 601.

In case of a continued rotation of the lever 501 in a first rotation direction D, in case of no insertion into the tibial plate, the extension from the adapter parts 410 and 430 would decrease.

In case the removal guide is inserted into the tibial plate, the elastic element 601 would slightly decompress forcing the continuous rotation of level 501. This continuous rotation is limited by the end position 411b of the slot 505. This end position locks the removal guide firmly to the tibial plate due to the compressed elastic element 601, which creates on side the compressive forces against the walls of the tibial plate and on the other side creates a force on the lever 501 in first rotation direction.

Figure 45:
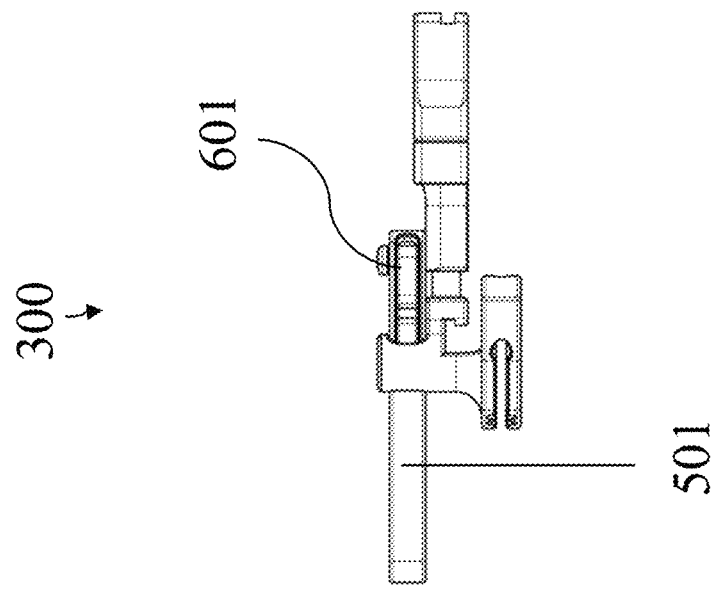
FIG. 45 represent a lateral view of the implant removal tool of FIG. 44.
Figure 44:
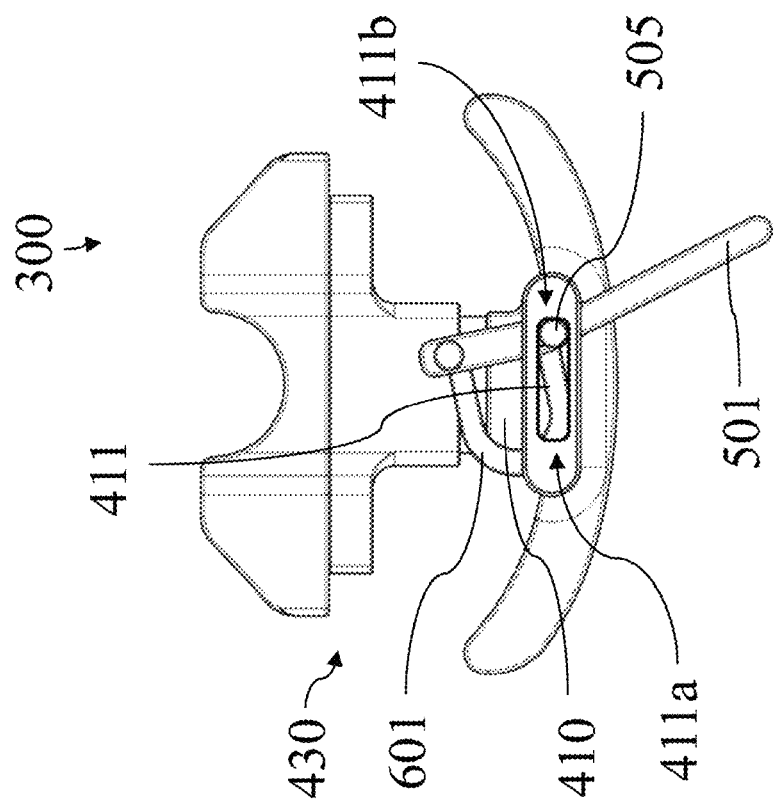
FIG. 44 represent a prospective view of the implant removal tool of figure in a locked configuration.

FIGS. 44 and 45 show tool 300 in a blocked configuration with first and second adapter parts 410, 430 spaced each other, lever 501 comply rotated in first rotation direction D with the slider 505 abutting at second first slot extremity 411b and elastic element 601 maximally compressed into the second slot 412.

To unblock the removal guide from the tibial plate a force needs to be applied to the lever 501 in counterrotation, which needs to compensate the compressive force of the elastic element and to move the lever 501 in the second rotation direction S.

The tibial baseplate achieves numerous advantages.

Advantageously, the disclosed tibial baseplate includes at least one porous portion seamlessly incorporated in a bulk solid portion without interface between porous and solid materials.

The continues transition between bulk solid portion and porous portions allows higher structural solidity and tensile resistance respects to tibial baseplates of prior art that has an interface between porous and solid materials that acts as a weakness of the structure.

Such an integral structure of the tibial baseplate reduces risks of delamination, shedding and galvanic effects typical of macro-rough coatings.

Advantageously, the tibial baseplate of the present invention could be completely manufactured by means of additive manufacturing, such as for example EBM.

The design of the tibial baseplate has been optimized by the Applicant carrying out accurate studies of the impact on micromotion (i.e. implant primary stability) and load transfer to the adjacent bone (i.e. stress shielding of the bone) of thickness and distribution of porous portions in the bulk solid portion; and position, material and quantity of stabilization elements.

More particularly, in a specific study a fluoroscopic study has been carried out to patients with knee prosthesis including femoral component, tibial liner and tibial plate, underwent to evaluate the biomechanics and kinematics of the prosthesis.

In parallel, a model database of tibial bones was created based of patients undergoing a total knee prosthesis. This step has been suitable because normally bone databases reports only the structure of healthy bones.

However, the load transfer of a healthy bone is different from those of patients undergoing Total Knee Arthroplasty. With these two inputs, physiological load condition of patients having already a prosthesis with the same design and having bone models with mechanical properties corresponding to bones whose demonstrate the defects causing a TKA, a series of finite element simulations were done considering modular and monolithic tibial baseplates in titanium with or without porous portion; different thickness, friction coefficient, and distribution of porous portions; shape, material, position and type of stabilization attachments.

The final design of the tibial baseplate described above is the optimum for reducing micromotion and stress shielding resulting in a uniform stress distribution and low micromotion, and avoiding interference with cortical bone of stabilization elements in order to keep the structural integrity of the bone and not to compromise the stability.

More particularly, the tibial baseplate of the present invention is of the modular type. This type is stiffer than monolithic type and thus determines less micromotions.

Furthermore, advantageously the tibial baseplate includes at least one porous portion having a high friction and a thickness of at least 1.2 mm that guarantee an overall elasticity and stiffness of the tibial baseplate optimizing the bone ingrowth conditions and reducing the micromotion.

The distribution of the porous portion also contributes to the elasticity and stiffness of the plate and it is optimized based on physical loading.

The presence of solid material between porous portion increase structural strength of the whole plate. More particularly, the location of solid zones is chosen to maximize the static and fatigue strength of the baseplate.

From the performed simulations emerged that antero-posterior location of stabilization elements has more influence than medio-later location.

Thus, the tibial baseplate of the present disclosure is provided with two pegs located in the posterior area and almost in the center of the correspondent condylar area. Posterior location also results in more physiological load transfer.

Furthermore, the Applicant has defined optimum linear distance in medio-later direction between the two posterior pegs for different baseplate sizes. See table below.

| Size | #1 | #2 | #3 | #4 | #5 | #6 | #7 | #8 | #9 | #10 |
|---|---|---|---|---|---|---|---|---|---|---|
| ML in mm | 24.7 | 27.9 | 31.3 | 34.7 | 38.4 | 42.2 | 46.1 | 49.6 | 50.1 | 50.7 |
| ML in % | 40.95% | 44.3% | 47.7% | 50.8% | 53.9% | 56.8% | 59.6% | 61.6% | 59.8% | 58% |

Furthermore, the Applicant has also defined optimum location of the posterior pegs in antero-posterior direction. More particularly, posterior pegs are located at 55% of the antero-posterior width of the baseplate.

This positioning contributes to minimize micromotions while reducing the risk of penetrating the posterior cortex of the tibia.

The pegs are made in porous material that was seen to contributes to reduce micromotions and better load transfer than solid pegs.

At least one anterior stabilization element is also advantageously provided to help reduce micromotion, More particularly anterior lift off due to posterior loads. It is a spike located anteriorly in a central position having at least a tip made in solid material in order to guarantee fully seating and in consequence bone ingrowth underneath the tibial baseplate.

The pegs and spikes made of porous materials could be also easily cut by means of an implant removal tool such as the one described hereabove.

The implant removal tool described advantageously includes simply and compact structure that allows rapid and effective coupling to the tibial baseplate and let stabilization elements be cut in in few seconds (less than 1 min) making little rubbles.

More particularly, the implant removal tool includes an adapter to be fixed into a seat of the tibial baseplate having two part that could be relatively moved away from each other to abut agents the peripheral walls of the seat.

The implant removal tool also advantageously includes a slide mechanism and locking means to respectively move the adapter's parts and lock them into the seat firmly locking implant removal tool into the tibial baseplate allowing to withstand forces during the removal procedure and the vibration of the saw blade during the cutting of stabilization elements.

Obviously, a skilled person, with the purpose of meeting contiguous and specific needs, may apply to the above-mentioned invention numerous changes and variants, all however within the scope of protection of the invention defined by the following claims.

What is claimed is:

1. A tibial baseplate for tibial component of a knee prosthesis comprising:
    a bulk solid portion comprising a proximally facing surface adapted to accommodate a bearing element for the articulation of a femoral component of said knee prosthesis; and
    a plurality of porous portions to allow bone ingrowth, being integral with said bulk solid portion and having a porous portion contacting surface opposite to said proximally facing surface adapted to contact a proximal tibia;
    wherein said plurality of porous portions are seamlessly incorporated in said bulk solid portion, wherein said plurality of porous portions are embedded into the bulk solid portion and are separated from each other by a solid non-porous part of the bulk solid portion such that each porous portion is surrounded by solid non-porous material of the bulk solid portion except for the porous portion contact surface that is adapted to contact the proximal tibia; and
    wherein said tibial baseplate is completely manufactured by means of additive manufacturing.

2. The tibial baseplate according to claim 1, wherein said plurality of porous portions have a thickness between 0.8 and 1.2 mm.

3. The tibial baseplate according to claim 1, comprising at least one stabilization element distally extending from said plurality of porous portions; said at least one stabilization element being adapted to be inserted into said proximal tibia.

4. The tibial baseplate according to claim 3, wherein said at least one stabilization element is located anteriorly the tibial baseplate to reduce micromotion and avoid lift off from tibial baseplate due to a posterior load when it is implanted.

5. The tibial baseplate according to claim 4, wherein said at least one stabilization element comprises a base body made in a porous material and a tip made in a solid material; said solid material facilitating insertion into the proximal tibia and limiting the bone ingrowth at said tip.

6. The tibial baseplate according to claim 3, wherein two stabilization elements are located posteriorly with regards to a frontal plane of the tibial baseplate and aligned in medio-lateral direction; said two stabilization elements being separated by a linear distance that varies depending on a size of the tibial baseplate.

7. The tibial baseplate according to claim 6, wherein the two stabilization elements are located at least at 55% of an antero-posterior width of the baseplate.

8. The tibial baseplate according to claim 3, wherein said stabilization element is completely made in a porous material.

9. The tibial baseplate according to claim 1, having a shape symmetrical respect to a central sagittal plane.

10. The tibial baseplate according to claim 1, wherein said plurality of porous portions define a pattern symmetrical respect to a central sagittal plane.

11. A tibial component for a knee prosthesis comprising the tibial baseplate according to claim 1 and further comprising a bearing element adapted to be accommodated on the proximally facing surface of said tibial baseplate.

12. The tibial baseplate according to claim 1, wherein the plurality of porous portions are made of a single material that is same as the solid non-porous material of the bulk solid portion.

13. A method for manufacturing a tibial baseplate, comprising:
  manufacturing the tibial baseplate layer by layer by additive manufacturing;
  wherein the tibial baseplate is configured for tibial component of a knee prosthesis;
  wherein the tibial baseplate comprises:
    a bulk solid portion comprising a proximally facing surface adapted to accommodate a bearing element for the articulation of a femoral component of said knee prosthesis; and
    a plurality of porous portions to allow bone ingrowth, being integral with said bulk solid portion and having a porous portion contacting surface opposite to said proximally facing surface adapted to contact a proximal tibia;
  wherein said plurality of porous portions are seamlessly incorporated in said bulk solid portion, wherein said plurality of porous portions are embedded into the bulk solid portion and are separated from each other by a solid non-porous part of the bulk solid portion such that each porous portion is surrounded by solid non-porous material of the bulk solid portion except for the porous portion contact surface that is adapted to contact the proximal tibia; and
  wherein said plurality of porous portions are embedded into the bulk solid portion.

14. The method for manufacturing according to claim 13, comprising manufacturing by Electron Beam Melting (EBM).

15. The method for manufacturing according to claim 13, wherein said tibial baseplate is made in titanium or titanium alloy.

* * * * *